US007588769B2

(12) United States Patent
Kawaoka

(10) Patent No.: US 7,588,769 B2
(45) Date of Patent: Sep. 15, 2009

(54) VIRUSES ENCODING MUTANT MEMBRANE PROTEIN

(75) Inventor: Yoshihiro Kawaoka, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/827,995

(22) Filed: Apr. 20, 2004

(65) Prior Publication Data

US 2004/0219170 A1 Nov. 4, 2004

Related U.S. Application Data

(60) Provisional application No. 60/464,776, filed on Apr. 23, 2003, provisional application No. 60/465,328, filed on Apr. 24, 2003.

(51) Int. Cl.

| | |
|---|---|
| *A61K 39/145* | (2006.01) |
| *C12N 7/00* | (2006.01) |
| *C12N 7/01* | (2006.01) |
| *C12N 15/44* | (2006.01) |
| *C12N 15/86* | (2006.01) |
| *C12N 5/10* | (2006.01) |
| *C12N 7/04* | (2006.01) |
| *A61K 39/295* | (2006.01) |

(52) U.S. Cl. ................. 424/209.1; 435/235.1; 435/236; 435/320.1; 435/325; 424/206.1; 424/199.1

(58) Field of Classification Search ............. 424/209.1, 424/206.1, 199.1; 435/5, 235.1
See application file for complete search history.

(56) References Cited

U.S. PATENT DOCUMENTS

| | | | | |
|---|---|---|---|---|
| 5,994,526 | A | 11/1999 | Meulewaeter et al. | |
| 6,194,546 | B1 * | 2/2001 | Newton et al. | 530/350 |
| 6,872,395 | B2 | 3/2005 | Kawaoka | |
| 2004/0063141 | A1 * | 4/2004 | Lok | 435/6 |
| 2005/0232950 | A1 | 10/2005 | Kawaoka | |
| 2006/0246092 | A1 * | 11/2006 | Neirynck et al. | 424/209.1 |
| 2007/0231348 | A1 | 10/2007 | Kawaoka et al. | |

FOREIGN PATENT DOCUMENTS

| | | | |
|---|---|---|---|
| WO | WO-96/10632 | A1 | 4/1996 |
| WO | WO-96/40955 | A1 | 12/1996 |
| WO | WO-00/53786 | A1 | 9/2000 |
| WO | WO-01/79273 | A2 | 10/2001 |
| WO | WO-0179273 | A3 | 10/2001 |
| WO | WO-04/094466 | A2 | 11/2004 |

OTHER PUBLICATIONS

Basler et al., "Mutation of Neuraminidase Cysteine Residues Yields Temperature-Sensitive Influenza Viruses," Journal of Virology, vol. 73, No. 10, pp. 8095-8103 (1999).*

Mitnaul et al., "The Cytoplasmic Tail of Influenza A Virus Neuraminidase (NA) Affects NA Incorporation into Virions, Virion Morphology, and Virulence in Mice but is not essential for Virus Replication," Journal of Virology, vol. 70, No. 2, pp. 873-879 (1996).*

Muster et al., "An influenza A virus containing influenza B virus 5' and 3' noncoding regions on the neuraminidase gene is attenuated in mice," Proc. Natl. Acad. Sci. Vo. 88, pp. 5177-5181 (1991). □□ □□.*

Wagner et al., "Interdependence of Hemagglutinin Glycosylation and Neuraminidase as Regulators of Influenza Virus Growth: a Study by Reverse Genetics," Journal of Virology, vol. 74, No. 14 pp. 6316-6323 (2000).*

Kochendorfer et al., "Total Chemical Synthesis of the Integral Membrane Protein Influenza A Virus M2: Role of its C-Terminal Domain in Tetramer Assembly," Biochemistry 38, pp. 11905-11913 (1999).*

Zebedee et al., "Characterization of the Influenza Virus M2 Integral Membrane Protein and Expression at the Infected-Cell Surface from Clined cDNA," Journal of Virology, vol. 56, No. 2, pp. 502-511 (1985).*

"1.A.32 The Type B Influenza Virus NB Channel (NB-C) Family", *Transport Protein Database.* (University of California, San Diego, The Sailer Laboratory Bioinformatics Group) http://www.web.archive.org/web/20030131105525 4/http://tcdb.ucsd.edu/tcdb/tcfamilybrowse.php?tcname=1.A.32. (Archived Jan. 31, 2003), 1 pg.

"International Search Report for corresponding PCT Application PCT/US2004/012050", (Feb. 2005), 8 pgs.

"The Integral Membrane Proteins of Influenza A, B, and C Viruses", *The Influenza Sequence Database*, http://www.flu.lanl.gov/review/fluc.review2.html, (Observed Feb. 26, 2003), 1 pg.

Author Unknown, "New Approaches to Influenza Vaccine", *Medscape—Infections in Medicine. http://www.medscape.com/viewarticle/417404*_3, (Observed Feb. 26, 1003), 4 pgs.

Castrucci, Maria R., et al., "Reverse Genetics System for Generation of an Influenza A Virus Mutant Containing a Deletion of the Carboxyl-Terminal Residue of M2 Protein", *J. of Virology*, 69(5), (May 1995), 2725-2728.

Duff, K. C., et al., "The Secondary Structure of Influenza A M2 Transmembrane Domain", *FEBS Letters*, 311(3), (Oct. 1992), pp. 256-258.

Duff, K. C., et al., "The Transmembrane Domain of Influenza A M2 Protein Forms Amantadine-Sensitive Proton Channels in Planar Lipid Bilayers", *Vilology*, 190(1), (Sep. 1992), pp. 485-489.

Grambas, S., et al., "Influence of Amantadine Resistance Mutations on the pH Regulatory Function of the M2 Protein of Influenza A Viruses", *Virology*, 191 (2), (Dec. 1992), pp. 541-549.

Hatta, M. , et al., "The NB Protein of Infuenza B Virus is not Necessary for Virus Replication in Vitro", *Journal of Virology*, 77(10), (May, 2003), 6050-6054.

Hay, A. J., et al., "The Role of the M2 Protein in Influenza A Virus Infection", *Proceedings of the International Conference on Options for the Control of Influenza*, Courchevel, (1992),pp. 281-288.

Helenius, A. , "Unpacking the Incoming Influenza Virus", *Cell*, 69, (May 1992), pp. 577-578.

(Continued)

*Primary Examiner*—Mary E Mosher
(74) *Attorney, Agent, or Firm*—Schwegman, Lundberg & Woessner, P.A.

(57) ABSTRACT

A method to prepare viruses with a mutant membrane protein gene, and viruses obtained by the method, are provided.

40 Claims, 27 Drawing Sheets

OTHER PUBLICATIONS

Hiromoto, Y., et al., "Phylogenetic Analysis of the Three Polymerase Genes (PB1, PB2 and PA) of Influenza B Virus", *Journal of General Virology*, 81, (Apr., 2000), 929-937.

Hoffmann, E., et al., "Rescue of Influenza B Virus from Eight Plasmids", *Proceedings of the National Academy of Sciences of USA, National Academy of Science*, vol. 99(17), (2002), 11411-11416.

Holsinger, L. J., et al., "Influenza A Virus $M_2$ Ion Channel Protein: a Structure-Function Analysis", *Journal of Virology*, 68 (3), (1994), pp. 1551-1563.

Hunt, R., "Virology—Chapter Eight—Vaccines: Past Successes and Future Prospects", *Microbiology and Immunology On-Line*, http://www.med.sc.edu:85/lecture/vaccines.htm, Observed Feb. 26, 2003, 15 pgs.

Krystal, M., et al., "Influenza B/Lee/40, hemagglutinin (seg 4), complete segment.", *Database EM VI E.B.I. Hinxton U.K.*, (Apr. 25, 1990).

Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.

Mckimm, J. L., et al., "Mutations in a Conserved Residue in the Influenza Virus Neuraminidase Active Site Decreases Sensitivity to Neu5Ac2en-Derived Inhibitors", *Journal of Virology*, 72(3), (1998), 2456-2462.

Mena, I., et al., "Rescue of a Synthetic Choramphenicol Acetyltransferase RNA into influenza Virus-Like Particles Obtained From Recombinant Plasmids", *J. of Virology*, 70(8), (Aug. 1996), 5016-5024.

Neirynck, S., "A Universal Influenza A Vaccine Based on the Extracellular Domain of the M2 Protein", *Nature Medicine*, 5 (10), (Oct. 1999), pp. 1157-1163.

Neumann, G., et al., "Generation of Influenza A Viruses Entirely From Cloned cDNAs", *Proc. Natl Acad. Sci.*, 96, (Aug., 1999), 9345-9350.

Neumann, G., et al., "Plasmid-Driven Formation of Influenza Virus-Like Particles", *J. of Virology*, 74(1), (Jan. 2000), 547-551.

Neumann, G., et al., "RNA Polymerase I-Mediated Expression of Influenza Viral RNA Molecules", *Virology*, 202(1), (Jul. 1994), 477-479.

Park, E. K., et al., "The M2 Ectodomain is Important for its incorporation into Influenza A Virions", *J. of Virology*, 72(3), (Mar. 1998), 2449-2455.

Pekosz, A., et al., "Influenza C Virus CM2 Integral Membrane Glycoprotein is Produced From a Polypeptide Precursor by Cleavage of an Internal Signal Sequence", *PNAS*, 95, (Oct. 1998), 13233-13238.

Piller, S C., et al., "Vpr Protein of Human Immunodeficiency Virus Type 1 Forms Cation-Selective Channels in Planar Lipid Bilayers", *PNAS*, 93, (1996),111-1115.

Pinto, L. H., et al., "Influenza Virus $M_2$ Protein Has Ion Channel Activity", *Cell*, 69, (May 1992). pp. 517-528.

Pleschka, Stephan, et al., "A Plasmid-Based Reverse Gentics System for Influenza A Virus", *J. of Virology*, 70(6), (Jun. 1996), 4188-4192.

Sansom, M. S., et al., "Influenza virus $M_2$ Protein: a Molecular Modelling Study of the Ion Channel", *Protein Engineering*, 6 (1), (1993), pp. 65-74.

Shaw, M., et al., "Influenza B/lee/40, neuraminidase & nb (seg 6) rna", *Database EM VI E.B.I. Hinxton U.K.*, (Jun. 13, 1985).

Skehel, J. J., et al., "On the Mechanism of Inhibition of Influenza Virus Replication by Amantadine Hydrochloride", *The Journal of General Virology*, 38 (1), (1977), pp. 97-110.

Sugrue, R. J., et al., "Specific Structural Alteration of the Influenza Haemagglutinin by Amantadine", *The EMBO Journal*, 9 (11), (1990), pp. 3469-3476.

Sugrue, R. J., et al., "Structural Characteristics of the M2 Protein of Influenza A Viruses: Evidence That It Forms a Tetrameric Channel", *Virology*, 180, (1991), pp. 617-624.

Sunstrom, N. A., et al., "Ion Channels formed by NB, an influenza B virus Protein", *J. of Membrane Biology*, 150, (Dec. 1996), 127-132.

Sweet, T.M., et al., "Creation of Amantadine Resistant Clones of Influenza Type A Virus Using a New Transfection Procedure", *J of Virological Methods*, vol. 69, XP002196650, (1997), 103-111.

Takeuchi, K., et al., "Influenza Virus $M_2$ Protein Ion Channel Activity Stabilizes the Native Form of Fowl Plague Virus Hemagglutinin during Intracellular Transport", *Journal of Virology*, 68 (2), (Feb. 1994), pp. 911-919.

Wang, C., et al., "Ion Channel Activity of Influenza A Virus $M_2$ Protein: Characterization of the Amantadine Block", *Journal of Virology*, 67 (9), (Sep. 1993), pp. 5585-5594.

Watanabe, T., et al., "Influenza A Virus with Defective M2 Ion Channel Activity as a Live Vaccine", *Virology*, 299(2), (Aug. 1, 2002), 266-270.

Krystal, M., et al., "Influenza B/Lee/40, hemagglutinin (seg 4), complete segment.", *Database Accession* No. KO0423, (Apr. 25, 1990).

Shaw, M., et al., "Influenza B/Lee/40, neuraminidase & nb (seg 6)rna", *Database accession* No. J02095, (Jun. 13, 1985).

Watanabe, T., et al., "Influenza A virus with defective M2 ion channel activity as a live vaccine", *Virology*, 299(2), (2002), 266-270.

"U.S. Appl. No. 09/834,095, Advisory Action mailed Jan. 8, 2004", 3 pgs.

"U.S. Appl. No. 09/834,095, Amendment and Response filed Nov. 26, 2003 to Final Office Action mailed Aug. 26, 2003", 10 pgs.

"U.S. Appl. No. 09/834,095, Amendment and Response filed Feb. 4, 2003 to Office Action mailed Nov. 4, 2002", 14 pgs.

"U.S. Appl. No. 09/834,095, Amendment and Response filed Jun. 18, 2004 to Office Action mailed Apr. 20, 2004", 11 pgs.

"U.S. Appl. No. 09/834,095, Final Office Action mailed Aug. 26, 2003", 12 pgs.

"U.S. Appl. No. 09/834,095, Non-Final Office Action mailed Nov. 4, 2002", 12 pgs.

"U.S. Appl. No. 09/834,095, Notice of Allowance mailed Sep. 27, 2004", 13 pgs.

"U.S. Appl. No. 09/834,095, Office Action mailed Apr. 20, 2004", 11 pgs.

"U.S. Appl. No. 09/834,095, Response filed Jun. 12, 2003 to Restriction Requirement mailed Apr. 22, 2003", 2 pgs.

"U.S. Appl. No. 09/834,095, Response filed Aug. 1, 2002 to Restriction Requirement mailed Jul. 1, 2002", 3 pgs.

"U.S. Appl. No. 09/834,095, Restriction Requirement mailed Apr. 22, 2003", 5 pgs.

"U.S. Appl. No. 09/834,095, Restriction Requirement mailed Jul. 1, 2002", 9 pgs.

"U.S. Appl. No. 09/834,095, Supplemental Amendment filed Aug. 4, 2004", 7 pgs.

"U.S. Appl. No. 11/043,768, Amendment and Response filed Mar. 10, 2008 to Office Action mailed Nov. 28, 2007", 12 pgs.

"U.S. Appl. No. 11/043,768, Response filed Sep. 13, 2007 to Restriction Requirement mailed Mar. 13, 2007", 10 pgs.

"U.S. Appl. No. 11/043,768, Restriction Requirement mailed Mar. 13, 2007", 9 pgs.

"U.S. Appl. No. 11/043,768, Non-Final Office Action mailed Nov. 28, 2007", 9 pgs.

"U.S. Appl. No. 11/043,768 Final Office Action mailed Jun. 27, 2008", 8 pgs.

"Australian Patent Application No. 2001255336, Examiner's First Report mailed Feb. 16, 2005", 2 pgs.

"Australian Patent Application No. 2001255336, Response filed Aug. 23, 2005 to Examiner's First Report dated Feb. 16, 2005", 10 pgs.

"Chinese Patent Application No. 200480017037, First Office Action dated May 25, 2007", 10 pgs.

"Chinese Patent Application No. 200480017037, Response filed Oct. 30, 2007 to First Office Action dated May 25, 2007", 26 pgs.

"European Application 04750333.9, Communication dated Oct. 12, 2006", 6 pgs.

"European Application 04750333.9, Communication dated Dec. 8, 2006", 4 pgs.

"European Application 04750333.9, Communication dated Apr. 11, 2008", 6 pgs.

"European Application 04750333.9, Response filed Oct. 4, 2007 to Communication dated Dec. 8, 2006", 42 pgs.

"European Application 04750333.9, Response filed Nov. 21, 2006 to Communication Oct. 12, 2006", 4 pgs.

"European Patent Application No. 01928486.8, Communication dated Aug. 10, 2007", 3 pgs.

"European Patent Application No. 01928486.8, Communication dated Sep. 20, 2005", 4 pgs.

"European Patent Application No. 01928486.8, Response filed Jan. 21, 2008 to Communication dated Aug. 10, 2007", 11 pgs.

"European Patent Application No. 01928486.8, Response filed Jan. 30, 2006 to Communication dated Sep. 20, 2005", 9 pgs.

"International Application No. PCT/US01/11963, Amendment filed Sep. 9, 2002 to Written Opinion dated Aug. 7, 2002", 12 pgs.

"International Application No. PCT/US01/11963, International Search Report mailed May 7, 2002", 5 pgs.

"International Application No. PCT/US01/11963, Written Opinion mailed Jun. 14, 2002", 2 pgs.

"International Application No. PCT/US01/11963, Written Opinion mailed Aug. 7, 2002", 6 pgs.

"International Application No. PCT/US2004/012050, International Search Report mailed Feb. 2, 2005", 8 pgs.

"International Application No. PCT/US2004/012050, Written Opinion mailed Feb. 2, 2005", 12 pgs.

"New Zealand Application No. 542935, Examination Report dated Feb. 25, 2008", 2 pgs.

"New Zealand Application No. 542935, Examination Report mailed Jun. 14, 2006", 2 pgs.

"New Zealand Application No. 542935, Response filed Jun. 30, 2008 to Examination Report dated Feb. 25, 2008", 32 pgs.

"New Zealand Application No. 542935, Response filed Aug. 7, 2007 to Examination Report dated Jun. 14, 2006", 18 pgs.

"New Zealand Application No. 542935, Voluntary Amendments filed Sep. 12, 2007", 10 pgs.

"Russian Federation Application No. 2005136233, First Office Action mailed Feb. 27, 2007", 5 pgs.

"Russian Federation Application No. 2005136233, Response filed Nov. 20, 2007 to Office Action", 18 pgs.

Betakova, T., et al., "The NB protein is an integral component of the membrane of influenza B virus.", *J Gen Virol.*, 77 (Pt 11), (Nov. 1996),2689-94.

Fischer, W. B., et al., "Viral ion channels: structure and function.", *Biochim Biophys Acta.*, 1561(1), (Mar. 19, 2002),27-45.

Fodor, E., et al., "Rescue of Influenza A Virus from Recombinant DNA", *Journal of Virology*, 73(11), (Nov. 1999),9679-9682.

Jackson, D., et al., "A reverse genetics approach for recovery of recombinant influenza B viruses entirely from cDNA.", *J Virol.*, 76(22), (Nov. 2002),11744-7.

Schickli, J.H., et al., "Plasmid-only rescue of influenza A virus vaccine candidates.", *Philos Trans R Soc Lond B Biol Sci.*, 356(1416), (Dec. 29, 2001),1965-1973.

"Canadian Patent Application Serial No. 2,406,180, Response filed Jan. 26, 2009 to Official Action mailed Sep. 9, 2008", 22 pgs.

"European Application Serial No. 04750333.9 Office Action mailed Jan. 22, 2009", 5 pgs.

"International Application Serial No. PCT/US01/11963, International Preliminary Examination Report mailed Oct. 15, 2002",13 pgs.

"Israel Application Serial No. 171372, Office Action Mailed Nov. 6, 2008", 12 pgs.

Bourmakina, S. V., et al., "Reverse genetics studies on the Filamentous morphology of influenza A Virus", *Journal of General Virology* (2003) 84., (2003),517-527.

"U.S. Appl. No. 11/043,768 Response filed Dec. 12, 2008 to Final Office Action mailed Jun. 27, 2008", 9 pgs.

"Canadian Patent Application Serial No. 2,406,180, Office Action mailed Sep. 9, 2008", 5 pgs.

"European Patent Application Serial No. 04750333.9 Response filed Oct. 21, 2008 to Communication mailed Apr. 11, 2008", 15 pgs.

"Indian Application No. 02082/KOLNP/2005 Examination Report mailed Mar. 17, 2008", 1 pg.

"Indian Application No. 02082/KOLNP/2005 Examination Report mailed Dec. 28, 2007", 1 pg.

"Indian Application No. 02082/KOLNP/2005 First Examination Report mailed Jan. 25, 2007", 9 pgs.

"Indian Application No. 02082/KOLNP/2005 Response filed Jan. 22, 2008 to Examination Report mailed Dec. 28, 2007", 13 pgs.

"Indian Application No. 02082/KOLNP/2005 Response filed Jun. 10, 2008 to Examination Report mailed Mar. 17, 2008", 3 pgs.

"Indian Application No. 02082/KOLNP/2005 Response filed Nov. 19, 2007 to First Examination Report mailed Jan. 25, 2007", 26 pgs.

"Korean Patent Application No. 10-2005-7020077 Notice of Preliminary Rejection mailed Jun. 28, 2007" (w/ English Translation), 9 pgs.

"Korean Patent Application No. 10-2005-7020077 Response filed Apr. 28, 2008 to Examination Report mailed Dec. 28, 2007" (w/ English Translation), 41 pgs. (Partial translation - claims only).

"Korean Patent Application No. 10-2005-7020077 Response filed Aug. 28, 2007 to Notice of Preliminary Rejection mailed Jun. 28, 2007" (w/ English Translation), 40 pgs. (Partial translation - claims only).

"Singapore Patent Application No. 200506858-0 Examination Report mailed Feb. 9, 2007", 4 pgs.

"Singapore Patent Application No. 200506858-0 Response filed Dec. 22, 2006 to Written Opinion mailed Jul. 26, 2006", 18 pgs.

"Singapore Patent Application No. 200506858-0 Written Opinion mailed Jul. 26, 2006", 8 pgs.

* cited by examiner

```
                                NB initiation codon
                                        ↓
                       40              60         165          175
B/Lee wild type    ...GCCAAAAATGAACAATGCTACC.....CTAAAATTTTA...
                                     ↑
                              NA initiation codon pPolBLeeNBstop#1   ...GCCAAAAGCGAACAATGCTACC.....CTTAAATTTTA...
                                                  Stop codon pPolBLeeNBstop#2   ...GCCAAAAGCG-ACAATGCTACC.....CTTAAATTTTA...

*
pPolBLeeNBstop#3   ...GCCAAAAGCGAAACAATGCTACC.....CTTAAATTTTA...
```

*FIG. 4*

B/Lee

>PB2
AGCAGAAGCGGAGCGTTTTCAAGATGACGTTGGCTAAAATTGAACTACTAAAGCAGCTGTTA
AGGGACAA
TGAAGC
CAAA
ACGGTGTTGAGACAGACAACGGTAGACCAATACAACATAATAAGAAAATTCAATACATCAAG
AATTGAAA
AGAACC
CTTC
ATTAAGAATGAAGTGGGCCATGTGTTCCAATTTTCCCTTAGCTCTGACCAAGGGTGATATGG
CAAATCGA
ATCCCC
TTGG
AATACAAGGGAATACAACTTAAAACAAATGCTGAAGACATAGGAACTAAAGGACAAATGTGTT
CAATAGC
AGCAGT
TACC
TGGTGGAATACATATGGGCCCATAGGGGATACTGAAGGGTTTGAAAAGGTCTACGAAAGCTT
TTTTCTCA
GAAAGA
TGAG
ACTTGACAATGCCACTTGGGGCCGAATGACCTTTGGCCCTGTTGAGAGAGTAAGAAAAAGA
GTACTACTA
AACCCG
CTCA
CCAAGGAAATGCCCCCAGATGAAGCGAGCAATGTAATAATGGAAATATTATTCCCTAAAGAA
GCAGGAAT
ACCAAG
AGAA
TCTACTTGGATACATAGAGAACTGATAAAAGAAAAAAGAGAAAAATTGAAGGGAACGATGATA
ACTCCCA
TTGTAC
TGGC

*FIG. 7A*

ATACATGCTTGAGAGAGAACTAGTTGCCCGAAGAAGGTTCCTGCCAGTAGCAGGAGCAACA
TCAGCAGAG
TTCATA
GAAA
TGCTACATTGCTTACAAGGTGAAAATTGGAGACAAATATATCATCCAGGAGGGAATAAACTAA
CTGAATC
TAGATC
TCAA
TCAATGATTGTAGCTTGCAGGAAGATAATCAGAAGATCAATAGTTGCATCAAACCCACTAGA
GCTAGCTG
TAGAGA
TTGC
AAATAAGACTGTGATAGACACTGAACCTTTAAAGTCATGTCTGGCAGCCCTAGATGGAGGTG
ATGTAGCC
TGTGAC
ATAA
TAAGAGCTGCATTAGGATTAAAAATTAGACAAAGACAAAGATTTGGGAGACTTGAACTAAAGA
GAATATC
AGGGAG
AGGA
TTCAAAAATGATGAAGAGATATTAATCGGAAACGGAACAATACAAAAGATTGGAATATGGGAC
GGAGAAG
AGGAAT
TCCA
TGTAAGATGTGGTGAATGCAGGGGGATATTGAAAAAAAGCAAAATGAGAATGGAAAAACTAC
TGATAAAT
TCAGCC
AAAA
AGGAGGACATGAAAGATTTAATAATCTTATGCATGGTATTTTCTCAAGACACCAGGATGTTCC
AAGGAGT
GAGAGG
AGAG
ATAAATTTTCTTAATCGAGCAGGCCAACTTTTATCCCCCATGTACCAACTCCAACGATACTTTT
TGAATA
GGAGCA
ATGA

*FIG. 7B*

CCTTTTTGATCAATGGGGATATGAGGAATCACCTAAAGCAAGTGAGCTACATGGGATAAATG
AATTAATG
AATGCA
TCTG
ACTATACATTGAAAGGGGTTGTAGTAACAAAAAATGTGATTGATGATTTTAGTTCTACTGAAA
CAGAAAA
AGTATC
TATA
ACAAAAAATCTTAGTTTAATAAAAAGGACTGGGGAAGTTATAATGGGAGCCAATGACGTAAGT
GAATTAG
AATCAC
AAGC
ACAGCTAATGATAACGTATGATACACCCAAGATGTGGGAAATGGGAACAACCAAAGAACTGG
TACAAAAC
ACTTAC
CAAT
GGGTGCTTAAAAATTTAGTAACATTGAAGGCTCAGTTTCTTTTGGGAAAAGAAGACATGTTCC
AATGGGA
TGCATT
TGAA
GCATTTGAAAGCATAATCCCTCAGAAGATGGCTGGTCAGTACAGTGGATTTGCAAGAGCAGT
GCTCAAAC
AAATGA
GAGA
CCAAGAGGTTATGAAAACTGACCAATTCATAAAATTGTTGCCTTTCTGTTTTTCGCCACCAAA
ATTAAGG
AGCAAT
GGAG
AGCCTTATCAATTTTTGAGGCTTATGCTGAAAGGAGGAGGGGAAAATTTCATCGAAGTAAGG
AAAGGGTC
CCCCTT
GTTC
TCCTACAATCCACAAACGGAAATCCTAACTATATGCGGCAGAATGATGTCATTAAAAGGAAAA
ATTGAGG
ATGAAG
AAAG

*FIG. 7C*

AAATAGATCAATGGGGAATGCAGTACTGGCAGGCTTTCTTGTTAGTGGCAAATATGACCCAG
ATCTTGGA
GATTTC
AAAA
CCATTGAGGAACTTGAAAGACTAAAACCGGGAGAAAAGCCAACATCTTACTTTACCAAGGA
AAGCCCGT
TAAAGT
AGTT
AAAAGGAAAAGATATAGTGCTTTATCCAATGATATTTCACAAGGGATTAAGAGACAAAGAATG
ACAGTTG
AGTCCA
TGGG
GTGGGCCTTGAGCTAATATAAATTTATCCATCAATTCAATAAATACAATTGAGTGAAAAATGCT
CGTGTT
TCTACT (SEQ ID NO: 1)

>PB1
AGCAGAAGCGGAGCTTTAAGATGAATATAAATCCATATTTTCTTTTCATAGATGTACCTATACA
GGCAGC
AATTTC
AACA
ACATTCCCATACACCGGTGTTCCCCCTTATTCTCATGGAACGGGAACAGGCTACACAATAGA
CACCGTGA
TTAGAA
CACA
CGAGTACTCAAACAAGGGAAAACAATACATTTCTGATGTTACAGGATGTGTAATGGTAGATC
CAACAAAT
GGGCCA
TTAC
CCGAAGACAATGAACCGAGTGCCTATGCACAATTGGATTGTGTTCTGGAGGCTTTGGATAGA
ATGGATGA
AGAACA
TCCA
GGTCTGTTTCAAGCAGCCTCACAGAATGCCATGGAGGCACTAATGGTCACAACAGTGGACA
AATTGACTC
AGGGGA
GACA

FIG. 7D

GACCTTTGATTGGACGGTGTGTAGAAACCAACCTGCTGCAACGGCACTGAACACAACAATAA
CCTCTTTT
AGGTTG
AATG
ATTTAAATGGAGCCGACAAGGGTGGATTAGTGCCCTTTTGCCAAGATATCATTGATTCATTAG
ACAAACC
TGAAAT
GATT
TTCTTCTCAGTAAAGAATATAAAGAAAAAATTGCCTGCTAAAAACAGAAAGGGTTTCCTTATAA
AAAGAA
TACCTA
TGAA
GGTAAAAGACAGAATAACAAGAGTGGAATACATCAAAAGAGCATTATCATTAAACACAATGAC
TAAAGAT
GCTGAA
AGAG
GCAAACTAAAAAGAAGAGCAATTGCCACCGCTGGGATACAAATCAGAGGATTTGTATTAGTA
GTTGAAAA
CTTGGC
TAAA
AATATCTGTGAAAATCTAGAGCAAAGTGGTTTACCCGTAGGTGGGAACGAAAAGAAGGCCAA
ACTATCAA
ATGCAG
TGGC
TAAAATGCTCAGTAATTGTCCACCAGGAGGGATCAGTATGACTGTGACAGGAGACAATACTA
AATGGAAT
GAATGC
TTAA
ATCCAAGAATCTTTTTGGCTATGACTGAAAGAATAACCAGAGACAGCCCAATTTGGTTCCGG
GATTTTTG
TAGTAT
AGCA
CCGGTCTTGTTCTCCAATAAAATAGCTAGATTGGGAAAAGGGTTCATGATAACAAGTAAAACA
AAAAGAC
TAAAAG
CTCA

*FIG. 7E*

AATACCTTGTCCCGATCTGTTTAATATACCATTAGAAAGATATAATGAAGAAACAAGGGCAAA
ACTGAAA
AAGCTA
AAAC
CTTTCTTCAATGAAGAAGGAACGGCATCTCTTTCGCCAGGAATGATGATGGGAATGTTTAATA
TGCTATC
TACAGT
ATTA
GGAGTAGCCGCACTAGGGATAAAAAACATTGGAAACAAAGAATACTTATGGGATGGACTGCA
GTCTTCCG
ATGATT
TTGC
TCTGTTTGTTAATGCAAAAGATGAAGAGACATGTATGGAAGGAATAAACGATTTTTACCGAAC
ATGTAAG
CTATTG
GGAA
TAAACATGAGCAAAAGAAAAGTTACTGTAATGAAACTGGGATGTTTGAATTTACCAGCATGT
TTTACAG
AGATGG
ATTT
GTATCTAATTTTGCAATGGAACTCCCTTCATTTGGAGTCGCTGGAGTGAATGAATCAGCAGA
CATGGCAA
TAGGAA
TGAC
AATAATAAAGAACAATATGATCAACAATGGGATGGGCCCAGCAACGGCACAAACAGCCATAC
AATTATTC
ATAGCT
GATT
ATAGATACACCTACAAATGCCACAGGGGAGATTCCAAAGTGGAAGGGAAGAGAATGAAAATT
ATAAAGGA
GCTATG
GGAA
AACACTAAAGGAAGAGATGGTCTATTAGTAGCAGATGGTGGGCCTAATCTTTACAATTTGAG
AAACCTGC
ATATTC
CAGA

*FIG. 7F*

AATAGTATTAAAATACAACATAATGGACCCTGAGTACAAAGGACGGTTACTGCATCCTCAAAA
TCCCTTT
GTAGGA
CATT
TGTCTATTGAGGGTATCAAAGAAGCAGATATAACACCTGCACATGGCCCAATAAAGAAAATG
GACTACGA
TGCGGT
ATCT
GGAACTCATAGTTGGAGAACCAAAAGGAACAGATCTATACTAAACACTGATCAGAGGAACAT
GATTCTTG
AGGAAC
AATG
CTACGCTAAGTGTTGCAACCTTTTTGAGGCTTGCTTTAACAGTGCGTCATACAGGAAACCAG
TAGGCCAG
CACAGC
ATGC
TTGAAGCTATGGCCCACAGATTAAGAATGGATGCACGACTGGACTATGAGTCAGGAAGGAT
GTCAAAAGA
GGATTT
CGAA
AAAGCAATGGCTCACCTTGGTGAGATTGGGTACATGTAAGCTCCGGAAATGTCTATGGGGTT
ATTGGTCA
TCGTTG
AATA
CATGCGGTGCACAAATGATTAAAATGAAAAAAGGCTCGTGTTTCTACT (SEQ ID NO: 2)

>PA
AGCAGAAGCGGTGCGTTTGATTTGCCACAATGGATACTTTTATTACAAAGAATTTCCAGACTA
CAATAAT
ACAAAA
GGCC
AAAAACACAATGGCAGAATTTAGTGAAGATCCTGAATTACAGCCAGCAGTACTATTCAACATC
TGCGTCC
ATCTGG
AGGT
CTGCTATGTAATAAGTGATATGAACTTTCTTGATGAGGAAGGAAAGACATATACAGCATTAGA
AGGACAA

*FIG. 7G*

GGAAAA
GAGC
AAAATTTGAGACCACAGTATGAAGTGATTGAGGGAATGCCAAGAAACATAGCATGGATGGTT
CAAAGATC
CTTAGC
CCAA
GAGCATGGAATAGAGACTCCAAGGTATCTGGCTGATTTATTTGATTATAAAACCAAGAGGTTT
ATCGAAG
TCGGAG
TAAC
AAAGGGATTGGCTGATGATTACTTTTGGAAAAAGAAAGAAAAGTTGGGGAATAGCATGGAAC
TGATGATA
TTCAGC
TATA
ATCAAGACTACTCGTTAAGTGATGAATCTTCATTGGATGAGGAAGGAAAAGGGAGAGTGCTA
AGCAGACT
CACAGA
ACTT
CAGGCTGAGTTAAGTTTGAAAAACCTATGGCAAGTTCTAATAGGGGAAGAAGAAATTGAAAA
AGGAATTG
ACTTCA
AACT
TGGACAAACAATATCTAAACTGAGGGATATATCTGTTCCAGCTGGTTTCTCCAATTTTGAAGG
GATGAGA
AGTTAC
ATAG
ACAACATAGACCCTAAAGGAGCAATAGAGAGAAATCTAGCAAGGATGTCTCCCTTAGTATCA
GTTACACC
CAAAAA
GTTG
AAATGGGAGGACCTGAGACCCATAGGGCCTCACATTTACAACCATGAGCTACCAGAAGTTC
CATATAATG
CCTTTC
TCCT
CATGTCTGATGAGTTGGGGCTGGCCAATATGACTGAAGGAAAGTCCAAGAAACCGAAGAC

CTAG
AAAGGTATTCAACACTACGTGATCAAACTGACCCAATATTGATAATGAAAAGCGAAAAAGCTA
ACGAAAA
CTTCTT
ATGG
AGGTTATGGAGGGACTGTGTAAATACAATAAGCAATGAGGAAACAGGCAACGAATTACAGAA
AACCAATT
ATGCCA
AGTG
GGCCACAGGAGATGGACTAACATACCAAAAAATAATGAAAGAAGTAGCAATAGATGACGAAA
CGATGTAC
CAAGAA
GAAC
CCAAAATACCCAATAAATGTAGAGTGGCTGCTTGGGTTCAGGCAGAGATGAATCTACTGAGT
ACTCTGAC
AAGTAA
AAGG
GCCCTGGATCTGCCAGAAATAGGGCCAGATGTAGCACCCGTGGAGCATGTAGGGAGTGAAA
GAAGGAAAT
ACTTTG
TTAA
TGAAATCAACTACTGTAAAGCCTCTACAGTTATGATGAAGTATGTACTTTTTCACACTTCATTA
TTAAAT
GAAAGC
AATG
CTAGTATGGGAAAATATAAAGTAATACCAATCACCAACAGAGTGGTAAATGGAAAAGGGGAA
AGCTTTGA
CATGCT
TTAT
GGTCTGGCGGTTAAGGGGCAATCTCATTTGCGGGGGGACACGGATGTTGTAACAGTTGTGA
CTTTCGAGT
TTAGTA
GTAC
AGATCCTAGAGTGGACTCAGGAAAGTGGCCAAAATATACTGTCTTTAAAATTGGCTCCCTATT
TGTGAGT
GGAAGA
GAAA

*FIG. 7I*

AACCTGTGTACCTATATTGCCGAGTGAATGGTACAAACAAAATCCAAATGAAATGGGGAATG
GAAGCTAG
AAGATG
TCTG
CTTCAATCAATGCAACAAATGGAGGCAATTGTTGATCAAGAATCATCGATACAAGGGTATGAT
ATGACCA
AAGCTT
GTTT
CAAGGGAGACAGAGTGAATAATCCCAAAACTTTCAGTATTGGGACTCAGGAAGGCAAACTAG
TAAAAGGG
TCCTTT
GGGA
AAGCACTAAGAGTAATATTCACCAAATGTTTGATGCATTATGTATTTGGAAATGCTCAATTGG
AGGGGTT
TAGTGC
CGAA
TCTAGGAGACTTCTACTGTTAATTCAGGCATTAAAAGACAGGAAGGGCCCTTGGGTATTTGA
CTTAGAGG
GAATGT
ACTC
TGGAGTAGAGGAATGTATTAGTAACAATCCTTGGGTAATACAGAGTGCATACTGGTTTAATGA
ATGGTTG
GGCATT
GAAA
AAGAAGGAAGTAAAGTGTTAGAATCAATAGATGAAATAATGGATGAATGAACGAAGGGCATA
GCGCTCAA
TTTAGT
ACTA
TTTTGTTCATTATGTATTTAAACATCCAATAAAAGAATTGAGAATTAAAAATGCACGTGTTTCT
ACT (SEQ ID NO: 3)

>HA
AGCAGAAGCGTTGCATTTTCTAATATCCACAAAATGAAGGCAATAATTGTACTACTCATGGTA
GTAACAT
CCAATG
CAGA

*FIG. 7J*

TCGAATCTGCACTGGGATAACATCGTCAAACTCACCTCATGTGGTTAAAACTGCCACTCAAG
GGGAAGTC
AATGTG
ACTG
GTGTGATACCACTAACAACAACACCTACTAGATCTCATTTTGCAAATCTCAAAGGAACACAGA
CCAGAGG
AAAACT
ATGC
CCAAACTGTTTTAACTGCACAGATCTGGACGTGGCCTTGGGCAGACCAAAATGCATGGGGA
ACATACCTT
CCGCAA
AAGT
CTCAATACTCCATGAAGTCAAACCTGTTACATCTGGATGCTTTCCTATAATGCACGACAGAAC
AAAAATC
AGACAA
CTAC
CTAATCTTCTCAGAGGATATGAAAACATCAGGTTATCAACCAGTAATGTTATCAATACAGAGA
CGGCACC
AGGAGG
ACCC
TACAAGGTGGGGACCTCAGGATCTTGCCCTAACGTTACTAATGGGAACGGCTTCTTCAACAC
AATGGCTT
GGGTTA
TCCC
AAAAGACAACAACAAGATAGCAATAAATCCAGTAACAGTAGAAGTACCATACATTTGTTCAGA
AGGGGAA
GACCAA
ATTA
CTGTTTGGGGGTTCCACTCTGATGACAAAACCCAAATGGAAAGACTCTATGGAGACTCAAAT
CCTCAAAA
GTTCAC
CTCA
TCTGCCAATGGAGTAACCACACATTATGTTTCTCAGATTGGTGGCTTCCCAAATCAAACAGAA
GACGAAG
GGCTAA
AACA

*FIG. 7K*

AAGCGGCAGAATTGTTGTTGATTACATGGTACAAAAACCTGGAAAAACAGGAACAATTGTTTA
TCAAAGA
GGCATT
TTAT
TGCCTCAAAAAGTGTGGTGCGCAAGTGGCAGGAGCAAGGTAATAAAAGGGTCCTTGCCTTT
AATTGGTGA
AGCAGA
TTGC
CTCCACGAAAAGTACGGTGGATTAAATAAAAGCAAGCCTTACTACACAGGAGAGCATGCAAA
GGCCATAG
GAAATT
GCCC
AATATGGGTGAAAACACCCTTGAAGCTGGCCAATGGAACCAAATATAGACCGCCTGCAAAAC
TATTAAAG
GAAAGA
GGTT
TCTTCGGAGCTATTGCTGGTTTCTTGGAAGGAGGATGGGAAGGAATGATTGCAGGTTGGCA
CGGATACAC
ATCTCA
TGGA
GCACATGGAGTGGCAGTGGCAGCAGACCTTAAGAGTACACAAGAAGCTATAAACAAGATAA
CAAAAAATC
TCAACT
CTTT
AAGTGAGCTAGAAGTAAAAAACCTTCAAAGACTAAGCGGAGCAATGAATGAGCTTCACGACG
AAATACTC
GAGCTA
GACG
AAAAAGTGGATGATCTAAGAGCTGATACAATAAGCTCACAAATAGAGCTTGCAGTCTTGCTTT
CCAACGA
AGGGAT
AATA
AACAGTGAAGATGAGCATCTTTTGGCACTTGAAAGAAAACTGAAGAAAATGCTGGGCCCCTC
TGCTGTAG
AAATAG
GGAA

*FIG. 7L*

TGGGTGCTTTGAAACCAAACACAAATGCAACCAGACTTGCCTAGACAGGATAGCTGCTGGCA
CCTTTAAT
GCAGGA
GATT
TTTCTCTTCCCACTTTTGATTCATTAAACATTACTGCTGCATCTTTAAATGATGATGGCTTGGA
TAATCA
TACTAT
ACTG
CTCTACTACTCAACTGCTGCTTCTAGCTTGGCTGTAACATTGATGATAGCTATCTTCATTGTC
TACATGG
TCTCCA
GAGA
CAATGTTTCTTGTTCCATCTGTCTGTGAGGGAGATTAAGCCCTGTGTTTTCCTTTACTGTAGT
GCTCATT
TGCTTG
TCAC
CATTACAAAGAAACGTTATTGAAAAATGCTCTTGTTACTACT (SEQ ID NO: 4)

>NA
AGCAGAAGCAGAGCATATTCTTAGAACTGAAGTGAACAGGCCAAAAATGAACAATGCTACCT
TCAACTGT
ACAAAC
ATTA
ACCCTATTACTCACATCAGGGGGAGTATTATTATCACTATATGTGTCAGCCTCATTGTCATAC
TTATTGT
ATTCGG
ATGT
ATTGCTAAAATTTTCATCAACAAAAACAACTGCACCAACAATGTCATTAGAGTGCACAAACGC
ATCAAAT
GCCCAG
ACTG
TGAACCATTCTGCAACAAAAGAGATGACATTTCCACCCCCAGAGCCGGAGTGGACATACCCT
CGTTTATC
TTGCCA
GGGC
TCAACCTTTCAGAAGGCACTCCTAATTAGCCCTCATAGGTTCGGAGAGATCAAAGGAAACTC
AGCTCCCT

*FIG. 7M*

TGATAA
TAAG
AGAACCTTTTGTTGCTTGTGGACCAAAAGAATGCAGACACTTTGCTCTGACCCATTATGCAG
CTCAGCCG
GGGGGA
TACT
ACAATGGAACAAGAAAGGACAGAAACAAGCTGAGGCATCTAGTATCAGTCAAATTGGGAAAA
ATCCCAAC
TGTGGA
AAAC
TCCATTTTCCACATGGCAGCTTGGAGCGGATCCGCATGCCATGATGGTAGAGAATGGACATA
TATCGGAG
TTGATG
GTCC
TGACAATGATGCATTGGTCAAAATAAAATATGGAGAAGCATATACTGACACATATCATTCCTA
TGCACAC
AACATC
CTAA
GAACACAAGAAAGTGCCTGCAATTGCATCGGGGGAGATTGTTATCTTATGATAACAGACGGC
TCAGCTTC
AGGAAT
TAGT
AAATGCAGATTTCTTAAAATTAGAGAGGGTCGAATAATAAAAGAAATACTTCCAACAGGAAGA
GTGGAGC
ACACTG
AAGA
GTGCACATGCGGGTTCGCCAGCAATAAAACCATAGAATGTGCCTGTAGAGACAACAGTTACA
CAGCAAAA
AGACCC
TTTG
TCAAATTAAATGTGGAAACTGATACAGCTGAAATAAGATTGATGTGCACAAAGACTTATCTGG
ACACTCC
CAGACC
GGAT
GATGGAAGCATAGCAGGGCCTTGCGAATCTAATGGAGACAAGTGGCTTGGAGGCATCAAAG
GAGGATTTG
TCCATC

*FIG. 7N*

AAAG
AATGGAATCTAAGATTGGAAGATGGTACTCCCGAACGATGTCTAAAACTAACAGAATGGGGA
TGGAACTG
TATGTA
AAGT
ATGATGGTGACCCATGGACTGACAGTGATGCTCTTACTCTTAGTGGAGTAATGGTTTCCATA
GAAGAACC
TGGTTG
GTAT
TCTTTTGGCTTCGAAATAAAGGACAAGAAATGTGATGTCCCTTGTATTGGGATAGAGATGGTA
CACGATG
GTGGAA
AAGA
TACTTGGCATTCAGCTGCAACAGCCATTTACTGTTTGATGGGCTCAGGACAATTGCTATGGG
ACACTGTC
ACAGGC
GTTG
ATATGGCTTTATAATAGAGGAATGGTTGGATCTGTTCTAAACCCTTTGTTCCTATTTTATTTGA
ACAGTT
GTTCTT
ACTA
GATTTAATTGTTTCTGAAAAATGCTCTTGTTACTACT (SEQ ID NO: 5)

>NP
AGCAGAAGCACAGCATTTTCTTGTGAGCTTCGAGCACTAATAAAACTGAAAATCAAAATGTCC
AACATGG
ATATTG
ACAG
TATAAATACCGGAACAATCGATAAAACACCAGAAGAACTGACTCCCGGAACCAGTGGGGCAA
CCAGACCA
ATCATC
AAGC
CAGCAACCCTTGCTCCGCCAAGCAACAAACGAACCCGAAATCCATCCCCAGAAAGGACAAC
CACAAGCAG
TGAAAC
CAAT

FIG. 70

ATCGGAAGGAAAATCCAAAAGAAACAAACCCCAACAGAGATAAAGAAGAGCGTCTACAACAT
GGTGGTAA
AACTGG
GTGA
ATTCTACAACCAGATGATGGTCAAAGCTGGACTTAATGATGACATGGAAAGGAATCTAATCC
AAAATGCA
CAAGCT
GTGG
AGAGAATCCTATTGGCTGCAACTGATGACAAGAAAACTGAATACCAAAAGAAAAGGAATGCC
AGAGATGT
CAAAGA
AGGG
AAAGAAGAAATAGACCACAGCAAGACAGGAGGCACCTTTTATAAGATGGTAAGAGATGATAA
AACCATCT
ACTTCA
GCCC
TATAAAAATTACCTTTTTAAAAGAAGAGGTGAAAACAATGTATAAGACCACCATGGGGAGTGA
TGGTTTC
AGTGGA
CTAA
ATCACATTATGATTGGACATTCACAGATGAACGATGTCTGTTTCCAAAGATCAAAGGCACTGA
AAAGGGT
TGGACT
TGAC
CCTTCATTAATCAGTACTTTTGCCGGAAGCACACTACCCAGAAGATCAGGTACAACTGGTGT
TGCAATCA
AAGGAG
GTGG
AACTTTAGTGGCAGAAGCCATCCGATTTATAGGAAGAGCAATGGCAGACAGAGGGCTACTG
AGAGACATC
AAGGCC
AAGA
CGGCCTATGAAAAGATTCTTCTGAATCTGAAAAACAAGTGCTCTGCGCCTCAACAAAAGGCT
CTAGTTGA
TCAAGT
GATC

*FIG. 7P*

GGAAGTAGGAACCCAGGGATTGCAGACATAGAAGACCTAACTCTGCTTGCCAGAAGCATGG
TAGTTGTCA
GACCCT
CTGT
AGCGAGCAAAGTGGTGCTTCCCATAAGCATTTATGCTAAAATACCTCAACTAGGATTCAATAT
CGAAGAA
TACTCT
ATGG
TTGGGTATGAAGCCATGGCTCTTTATAATATGGCAACACCTGTTTCCATATTAAGAATGGGAG
ATGACGC
AAAAGA
TAAA
TCTCAACTATTCTTCATGTCGTGCTTCGGAGCTGCCTATGAAGATCTAAGAGTGTTATCTGCA
CTAACGG
GCACCG
AATT
TAAGCCTAGATCAGCACTAAAATGCAAGGGTTTCCATGTCCCGGCTAAGGAGCAAGTAGAAG
GAATGGGG
GCAGCT
CTGA
TGTCCATCAAGCTTCAGTTCTGGGCCCCAATGACCAGATCTGGAGGGAATGAAGTAAGTGG
AGAAGGAGG
GTCTGG
TCAA
ATAAGTTGCAGCCCTGTGTTTGCAGTAGAAAGACCTATTGCTCTAAGCAAGCAAGCTGTAAG
AAGAATGC
TGTCAA
TGAA
CGTTGAAGGACGTGATGCAGATGTCAAAGGAAATCTACTCAAAATGATGAATGATTCAATGG
CAAAGAAA
ACCAGT
GGAA
ATGCTTTCATTGGGAAGAAAATGTTTCAAATATCAGACAAAAACAAAGTCAATCCCATTGAGA
TTCCAAT
TAAGCA
GACC

*FIG. 7Q*

ATCCCCAATTTCTTCTTTGGGAGGGACACAGCAGAGGATTATGATGACCTCGATTATTAAAG
CAATAAAA
TAGACA
CTAT
GGCTGTGACTGTTTCAGTACGTTTGGGATGTGGGTGTTTACTCTTATTGAAATAAATGTAAAA
AATGCTG
TTGTTT
CTAC
T (SEQ ID NO: 6)

>M
AGCAGAAGCACGCACTTTCTTAAAATGTCGCTGTTTGGAGACACAATTGCCTACCTGCTTTC
ACTAATAG
AAGATG
GAGA
AGGCAAAGCAGAACTAGCTGAAAAATTACACTGTTGGTTCGGTGGGAAAGAATTTGACCTAG
ATTCTGCT
TTGGAA
TGGA
TAAAAAACAAAAGGTGCCTAACTGATATACAAAAAGCACTAATTGGTGCCTCTATATGCTTTT
TAAAACC
CAAAGA
CCAA
GAAAGAAAAAGGAGATTCATCACAGAGCCCCTGTCAGGAATGGGAACAACAGCAACAAAGA
AGAAAGGCC
TAATTC
TAGC
TGAGAGAAAAATGAGAAGATGTGTAAGCTTTCATGAAGCATTTGAAATAGCAGAAGGCCACG
AAAGCTCA
GCATTA
CTAT
ATTGTCTTATGGTCATGTACCTAAACCCTGAAAACTATTCAATGCAAGTAAAACTAGGAACGC
TCTGTGC
TTTATG
CGAG
AAACAAGCATCGCACTCGCATAGAGCCCATAGCAGAGCAGCAAGGTCTTCGGTACCTGGAG
TAAGACGAG

*FIG. 7R*

AAATGC

AGAT

GGTTTCAGCTATGAACACAGCAAAGACAATGAATGGAATGGGAAAGGGAGAAGACGTCCAA

AAACTAGCA

GAAGAG

CTGC

AAAACAACATTGGAGTGTTGAGATCTCTAGGAGCAAGTCAAAAGAATGGAGAAGGAATTGCC

AAAGATGT

AATGGA

AGTG

CTAAAACAGAGCTCTATGGGAAATTCAGCTCTTGTGAGGAAATACTTATAATGCTCGAACCAC

TTCAGAT

TCTTTC

AATT

TGTTCTTTCATTTTATCAGCTCTCCATTTCATGGCTTGGACAATAGGGCATTTGAATCAAATAA

GAAGAG

GGGTAA

ACCT

GAAAATACAAATAAGGAATCCAAATAAGGAGGCAATAAACAGAGAGGTGTCAATTCTGAGAC

ACAATTAC

CAAAAG

GAAA

TCCAAGCCAAAGAAACAATGAAGAAAATACTCTCTGACAACATGGAAGTATTGGGTGACCAC

ATAGTAGT

TGAAGG

GCTT

TCAACTGATGAGATAATAAAAATGGGTGAAACAGTTTTGGAGGTGGAAGAATTGCAATGAGC

CCAATTTT

CACTGT

ATTT

CTTACTATGCATTTAAGCAAATTGTAATCAATGTCAGTGAATAAAACTGGAAAAAGTGCGTTG

TTTCTAC

T (SEQ ID NO: 7)

>NS

AGCAGAAGCAGAGGATTTATTTAGTCACTGGCAAACGGAAAGATGGCGGACAACATGACCA

CAACACAAA

*FIG. 7S*

TTGAGG

TGGG

TCCGGGAGCAACCAATGCCACTATAAACTTTGAAGCAGGAATTCTGGAGTGCTATGAAAGGT

TTTCATGG

CAAAGA

GCCC

TTGACTATCCTGGTCAAGACCGCCTACACAGACTAAAACGAAAATTAGAATCAAGAATAAAGA

CTCACAA

CAAGAG

TGAG

CCTGAGAATAAAAGGATGTCTCTTGAAGAGAGAAAAGCAATTGGGGTAAAAATGATGAAAGT

GCTTCTGT

TTATGG

ATCC

CTCTGCTGGAATTGAAGGGTTTGAGCCATACTGTGTGAAAAATCCCTCAACTAGCAAATGTC

CAAATTAC

GATTGG

ACCG

ATTACCCTCCAACCCCAGGAAAGTACCTTGATGACATAGAAGAAGAGCCGGAAAATGTCGAT

CACCCAAT

TGAGGT

AGTA

TTAAGGGACATGAACAATAAAGATGCACGACAAAAGATAAAGGATGAAGTAAACACTCAGAA

AGAGGGA

AATTCC

ATTT

GACAATAAAAAGGGATATACGTAATGTGTTGTCCTTGAGAGTGTTGGTGAACGGAACCTTCC

TCAAGCAC

CCTAAT

GGAG

ACAAGTCCTTATCAACTCTTCATAGATTGAATGCATATGACCAGAATGGAGGGCTTGTTGCTA

AACTTGT

TGCTAC

TGAT

GATCTTACAGTGGAGGATGAAAAAGATGGCCATCGGATCCTCAACTCACTCTTCGAGCGTTT

TGATGAAG

GACATT

*FIG. 7T*

CAAA
GCCAATTCGAGCAGCTGAAACTGCGGTGGGAGTCTTATCCCAATTTGGTCAAGAGCACCGA
TTATCACCA
GAAGAG
GGAG
ACAATTAGACTGGCCACGGAAGAACTTTATCTCTTGAGTAAAAGAATTGATGATAGTATATTG
TTCCACA
AAACAG
TAAT
AGCTAACAGCTCCATAATAGCTGACATGATTGTATCATTATCATTACTGGAAACATTGTATGA
AATGAAG
GATGTG
GTTG
AAGTGTACAGCAGGCAGTGCTTATGAATGTAAAATAAAAATCCTCTTGTTACTACT
(SEQ ID NO: 8)

*FIG. 7U*

VIRUSES ENCODING MUTANT MEMBRANE PROTEIN

CROSS-REFERENCE TO RELATED APPLICATIONS

The present application claims the benefit of the filing date of U.S. application Ser. No. 60/464,776, filed Apr. 23, 2003, and U.S. application Ser. No. 60/465,328, filed Apr. 24, 2003, the disclosures of which are incorporated by reference herein.

STATEMENT OF GOVERNMENT RIGHTS

This invention was made with a grant from the Government of the United States of America (grant AI-47446 from the National Institutes of Health). The Government may have certain rights in the invention.

BACKGROUND OF THE INVENTION

Cell membranes consist of a double layer of lipid molecules in which various proteins are embedded. Because of its hydrophobic interior, the lipid bilayer of cell membranes serves as a barrier to the passage of most polar molecules and therefore is crucial to cell viability. To facilitate the transport of small water-soluble molecules into or out of cells or intracellular compartments, such membranes possess carrier and channel proteins. Ion channels are essential for many cellular functions, including the electrical excitability of muscle cells and electrical signaling in the nervous system (reviewed by Alberts et al., 1994). They are present not only in all animal and plant cells, as well as microorganisms, but also have been identified in viruses (Ewart et al., 1996; Piller et al., 1996; Pinto et al., 1992; Schubert et al., 1996; Sugrue et al., 1990; Sunstrom et al., 1996), where they are thought to play an important role in the viral life cycle.

The influenza A virus is an enveloped negative-strand virus with eight RNA segments encapsidated with nucleoprotein (NP) (reviewed by Lamb and Krug, 1996). Spanning the viral membrane are three proteins: hemagglutinin (HA), neuraminidase (NA), and M2. The extracellular domains (ectodomains) of HA and NA are quite variable, while the ectodomain domain of M2 is essentially invariant among influenza A viruses. The life cycle of viruses generally involves attachment to cell surface receptors, entry into the cell and uncoating of the viral nucleic acid, followed by replication of the viral genes inside the cell. After the synthesis of new copies of viral proteins and genes, these components assemble into progeny virus particles, which then exit the cell (reviewed by Roizman and Palese, 1996). Different viral proteins play a role in each of these steps. In influenza A viruses, the M2 protein which possesses ion channel activity (Pinto et al., 1992), is thought to function at an early state in the viral life cycle between host cell penetration and uncoating of viral RNA (Martin and Helenius, 1991; reviewed by Helenius, 1992; Sugrue et al., 1990). Once virions have undergone endocytosis, the virion-associated M2 ion channel, a homotetrameric helix bundle, is believed to permit protons to flow from the endoscopes into the virion interior to disrupt acid-labile M1protein-ribonucleoprotein complex (RNP) interactions, thereby promoting RNP release into the cytoplasm (reviewed by Helenius, 1992). In addition, among some influenza strains whose HAs are cleaved intracellularly (e.g., A/fowl plagues/Rostock/34), the M2 ion channel is thought to raise the pH of the trans-Golgi network, preventing conformational changes in the HA due to conditions of low pH in this compartment (Hay et al., 1985; Ohuchi et al., 1994; Takeuchi and Lamb, 1994).

Evidence that the M2 protein has ion channel activity was obtained by expressing the protein in oocytes of *Xenopus laevis* and measuring membrane currents (Pinto et al., 1992; Wang et al., 1993; Holsinger et al., 1994). Specific changes in the M2 protein transmembrane (TM) domain altered the kinetics and ion selectivity of the channel, providing strong evidence that the M2 TM domain constitutes the pore of the ion channel (Holsinger et al., 1994). In fact, the M2 TM domain itself can function as an ion channel (Duff and Ashley, 1992). M2 protein ion channel activity is thought to be essential in the life cycle of influenza viruses, because amantadine hydrochloride, which blocks M2 ion channel activity (Hay et al., 1993), inhibits viral replication (Kato and Eggers, 1969; Skehel et al., 1978).

The genome of influenza B virus, a member of the family Orthomyxoviridae, consists of eight negative-strand RNA segments, which encode 11 proteins. Of these, nine are also found in influenza A virus: three RNA-dependent RNA polymerase subunits (PB1, PB2, and PA), hemagglutinin (HA), nucleoprotein (NP), neuraminidase (NA), matrix protein (M1), and two nonstructural proteins (NS1 and NS2). Two proteins, NB and BM2 are unique to influenza B virus. NB is encoded by RNA segment 6, which also encodes NA, while BM2 is encoded by segment 7.

The NB protein of influenza B virus is a type III integral membrane protein, expressed abundantly on the surface of virus-infected cells (Betakova et al., 1996; Shaw et al., 1983; Shaw et al., 1984), and is incorporated into virions (Betakova et al., 1996; Brassard et al., 1996). This small protein (100 amino acids) possesses an 18-residue N-terminal ectodomain, a 22-residue transmembrane domain, and a 60-residue cytoplasmic tail (Betakova et al., 1996; Williams et al., 1986). From previous studies measuring membrane currents, and by analogy with the M2 protein of influenza A virus (Fisher et al., 2000; Fisher et al., 2001; Sunstrom et al., 1996), NB was thought to function as an ion channel protein. However, the electrophysiological measurements of NB protein based on the lipid bilayer system are difficult to interrupt. That is, proteins and peptides containing hydrophobic domains, which are believed to lack ion channel activity in cells, can yield channel recordings in lipid bilayers (Lear et al., 1988; Tosteson et al., 1988; Tosteson et al., 1989). Moreover, in the studies of Fischer et al. (2001), and Sunstrom et al. (1996), amantadine was used to demonstrate the loss of channel activity by NB protein, despite the inability of this drug to inhibit influenza B virus replication. Thus, the available evidence challenges the notion that the NB protein has ion channel activity.

Immunity to viral infections depends on the development of an immune response to antigens present on the surface of infected cell or on the virions. If the surface viral antigens are known, successful vaccines can be produced. Although there may be several antigens present on the surface, only some of them produce neutralizing immunity. One method to produce a vaccine is to "attenuate" the virus. This is usually done by passing infectious virus into a foreign host and identifying strains that are super virulent. Normally, these super virulent strains in the foreign host are less virulent in the original host cell, and so are good vaccine candidates as they produce a good immune response in the form of humoral IgG and local IgA.

Generally, influenza vaccines have been prepared from live, attenuated virus or killed virus which can grow to high titers. Live virus vaccines activate all phases of the immune system and stimulate an immune response to each of the protective antigens, which obviates difficulties in the selective destruction of protective antigens that may occur during preparation of inactivated vaccines. In addition, the immunity produced by live virus vaccines is generally more durable, more effective, and more cross-reactive than that induced by inactivated vaccines. Further, live virus vaccines are less costly to produce than inactivated virus vaccines. However, the mutations in attenuated virus are often ill-defined and those mutations appear to be in the viral antigen genes.

Thus, what is needed is a method to prepare recombinant attenuated influenza virus for vaccines e.g., attenuated viruses having defined mutation(s).

SUMMARY OF THE INVENTION

The invention provides an isolated and/or purified recombinant influenza virus comprising a mutant membrane protein gene, e.g., a mutant integral membrane protein gene such as a mutant type III integral membrane protein gene, which does not encode a functional membrane protein or a functional portion thereof. The invention also provides an isolated and/or purified recombinant influenza virus which lacks a membrane protein gene. The lack of a functional membrane protein such as an integral membrane protein in a recombinant influenza virus provides for recombinant influenza viruses which replicate in vitro but are attenuated in vivo. In one embodiment, the recombinant virus comprises a mutant membrane protein gene which comprises one or more mutations which, when the gene is transcribed and/or translated in a cell, does not yield a functional membrane protein or a functional portion thereof. In another embodiment, the mutant membrane protein gene comprises at least two mutations relative to a corresponding membrane protein gene which encodes a functional membrane protein, wherein at least one of the mutations is not in a region corresponding to the transmembrane domain of the protein. For example, the mutant membrane protein gene, when transcribed and/or translated in a cell, does not yield a functional gene product, yields reduced, e.g., less than about 50%, 10%, 1%, or undetectable, levels of the wild-type membrane protein, and/or yields a mutant membrane protein with less than about 50%, preferably less than about 10%, and more preferably less than about 1%, the activity of the corresponding wild-type (functional) membrane protein, e.g., as a result of the absence of wild-type sequences at the C-terminus, i.e., a truncated membrane protein. In one embodiment of the invention, the mutant membrane protein gene encodes at least one amino acid substitution relative to the corresponding wild-type membrane protein. In one embodiment, the substitution(s) is at or within about 1 to 50 residues, or any integer in between, for instance, at or within 1 to 20 or at or within 1 to 3, residues, of the initiator methionine. In one preferred embodiment, at least one substitution is at the initiator methionine. In another embodiment, the mutant membrane protein gene has one or more stop codons at or within about 1 to 50 codons, or any integer in between, e.g., at or within 1 to 20 codons of the initiator codon. In yet another embodiment, the mutant membrane protein gene comprises one or more deletions of one or more nucleotides. In one embodiment, the mutant membrane protein gene comprises one or more deletions of one or more nucleotides at or within about 150 nucleotides, e.g., at or within 1, 2, 3 up to 150 nucleotides, or any integer in between, of the first codon in the coding region of the gene. In one embodiment, the mutant membrane protein gene comprises one or more insertions of one or more nucleotides. In one embodiment, the mutant membrane protein gene comprises one or more insertions of one or more nucleotides at or within about 150 nucleotides, e.g., at or within 1, 2, 3 up to 150 nucleotides, or any integer in between, of the first codon in the coding region of the gene. Such insertion(s) and/or deletion(s) preferably alter the reading frame of the membrane protein gene. In yet another embodiment, the mutant membrane protein gene comprises two or more mutations, e.g., two or more mutations including a nucleotide substitution in the initiator codon that results in a codon for an amino acid other than methionine, a nucleotide substitution that results in a stop codon at the initiation codon, a nucleotide substitution that results in a stop codon in the coding sequence, one or more nucleotide deletions in the coding sequence, one or more nucleotide insertions in the coding sequence, or any combination thereof. In one embodiment, the mutant membrane protein gene is in a vector and is operably linked to a promoter including, but not limited to, a RNA polymerase I promoter, e.g., a human RNA polymerase I promoter, a RNA polymerase II promoter, a RNA polymerase III promoter, a T7 promoter, and a T3 promoter. In another embodiment, the mutant membrane protein gene is in a vector and is linked to transcription termination sequences including, but not limited to, a RNA polymerase I transcription termination sequence, a RNA polymerase II transcription termination sequence, or a RNA polymerase III transcription termination sequence, or a ribozyme.

As described herein, influenza B knockout viruses were generated by reverse genetics and their growth characteristics and other properties tested both in vitro and in vivo. Mutants not expressing NB replicated as efficiently as the wild-type virus in cell culture, whereas in mice they showed restricted growth compared with findings for the wild-type virus. Thus, NB protein is not essential for influenza B virus replication in cell culture, but promotes efficient growth in mice. Given the attenuated growth of the NB knockout virus in vivo, but not in vitro, these mutant viruses may be useful in the development of live influenza vaccines.

Thus, the invention further provides a vaccine or immunogenic composition comprising a recombinant virus of the invention, and a method of using the vaccine or immunogenic composition to immunize a vertebrate or induce an immune response in a vertebrate, respectively. In one embodiment, the recombinant virus of the invention includes genes from influenza A virus. In another embodiment, the recombinant virus of the invention includes genes from influenza B virus. In yet another embodiment, the recombinant virus of the invention includes genes from influenza C virus. In a further embodiment, the recombinant virus of the invention includes one or more genes from influenza A virus, influenza B virus, influenza C virus, or any combination thereof. For instance, the recombinant virus may comprise a mutant NB gene derived from the NB gene of B/Lee/40, B/Shiga/T30/98, B/Mie/1/93, B/Chiba/447/98, B/Victoria/2/87, B/Yamanashi/166/98, B/Nagoya/20/99, B/Kouchi/193/99, B/Saga/S172/99, B/Kanagawa, B/Lusaka/432/99, B/Lusaka/270/99, B/Quebec/74204/99, B/Quebec/453/98, B/Quebec/51/98, B/Quebec/465/98 and B/Quebec/511/98 (Accession Nos. AB036873, AB03672, AB036871, AB036870, AB036869, AB036868, AB036867, AB036866, D14855, D14543, D14542, AB059251, AB059243, NC 002209, AJ419127, AJ419126, AJ419125, AJ419124, and AJ419123, the disclosures of which are specifically incorporated by reference herein). In one embodiment, the mutation(s) in the NB gene do not alter the sequence of the NA gene. In another embodiment, the mutation(s) in the NB gene also alter the sequence of the NA gene but yield a NA with substantially the same activity as the NA encoded by a corresponding non-mutated NA gene. As used herein, "substantially the same activity"

includes an activity that is about 0.1%, 1%, 10%, 30%, 50%, e.g., up to 100% or more, the activity of the corresponding full-length polypeptide.

Also provided is a method of preparing a recombinant influenza virus comprising a mutant membrane protein gene which does not encode a functional membrane protein or a functional portion thereof relative to a corresponding wild-type membrane protein gene. The method comprises contacting a host cell with a composition comprising a plurality of influenza vectors, including a vector comprising a mutant membrane protein gene, so as to yield recombinant virus. For example, for influenza B, the composition comprises: a) at least two vectors selected from a vector comprising a promoter operably linked to an influenza virus PA cDNA linked to a transcription termination sequence, a vector comprising a promoter operably linked to an influenza virus PB 1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising promoter operably linked to an influenza virus NP cDNA linked to a transcription termination sequence, a vector comprising a promoter operably linked to an influenza virus cDNA NA and NB linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein the sequence of the cDNA for NB comprises at least two mutations relative to a corresponding NB gene which encodes a functional NB membrane protein, one of which mutations is not in the transmembrane domain, the presence of which in the mutant gene, when the mutant gene is transcribed and translated in the host cell, does not yield a functional membrane protein or a functional portion thereof, and optionally yields a functional NA protein, and b) at least two vectors selected from a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, a vector comprising a promoter operably linked to a DNA segment encoding influenza virus NP, a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding influenza virus BM2, and a vector comprising a promoter operably linked to a DNA segment encoding influenza virus NS.

The invention further provides a composition comprising a plurality of vectors such as those described above, and a host cell contacted with such a composition or isolated recombinant virus of the invention, e.g., so as to yield infectious virus. Alternatively, the host cell may be contacted with each vector, or a subset of vectors, sequentially.

Further provided is an isolated and/or purified nucleic acid molecule (polynucleotide) encoding at least one of the proteins of influenza virus B/Lee/40, or a portion thereof, or the complement of the nucleic acid molecule. In one embodiment, the isolated and/or purified nucleic acid molecule encodes HA, NA, PB1, PB2, PA, NP, M, or NS, or a portion thereof having substantially the same activity as a corresponding polypeptide of one of SEQ ID NOs:1-8. As used herein, "substantially the same activity" includes an activity that is about 0.1%, 1%, 10%, 30%, 50%, e.g., up to 100% or more, the activity of the corresponding full-length polypeptide. In one embodiment, the isolated and/or purified nucleic acid molecule encodes a polypeptide having at least 80%, e.g., 90%, 92%, 95%, 97% or 99%, contiguous amino acid sequence identity to one of SEQ ID NOs. 1-8. In one embodiment, the isolated and/or purified nucleic acid molecule comprises a nucleotide sequence having at least 50%, e.g., 60%, 70%, 80% or 90% or more contiguous nucleic acid sequence homology to one of SEQ ID NOs. 1-8, or the complement thereof, and if homologous to coding sequences of one of SEQ ID NOs:1-8, encodes a polypeptide having at least 80%, e.g., 90%, 92%, 95%, 97% or 99%, contiguous amino acid sequence identity to one of SEQ ID NOs. 1-8. In another embodiment, the isolated and/or purified nucleic acid molecule encoding at least one of the proteins of influenza virus B/Lee/40, or a portion thereof, or the complement of the nucleic acid molecule, hybridizes to one of SEQ ID NOs. 1-8, or the complement thereof, under low stringency, moderate stringency or stringent conditions. For example, the following conditions may be employed: 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

The nucleic acid molecule of the invention may be employed to express influenza proteins, to prepare chimeric genes, e.g., with other viral genes including other influenza virus genes, and/or to prepare recombinant virus. Thus, the invention also provides isolated polypeptides, recombinant virus and host cells contacted with the nucleic acid molecules or recombinant virus comprising influenza virus B/Lee/40 sequences. Such polypeptides, recombinant virus and host cells may be used in medical therapy, e.g., to induce a protective immune response or in gene therapy.

BRIEF DESCRIPTION OF THE FIGURES

FIG. 1. Schematic diagram of established reverse genetics systems. In the RNP transfection method (A), purified NP and polymerase proteins are assembled into RNPs with use of in vitro-synthesized vRNA. Cells are transfected with RNPs, followed by helper virus infection. In the RNA polymerase I method (B), a plasmid containing the RNA polymerase I promoter, a cDNA encoding the vRNA to be rescued, and the RNA polymerase I terminator is transfected into cells. Intracellular transcription by RNA polymerase I yields synthetic vRNA, which is packaged into progeny virus particles upon infection with helper virus. With both methods, transfectant viruses (i.e., those containing RNA derived from cloned cDNA), are selected from the helper virus population.

FIG. 2. Schematic diagram of the generation of RNA polymerase I constructs. cDNAs derived from influenza virus were amplified by PCR, digested with BsmBI and cloned into the BsmBI sites of the pHH21 vector (E. Hoffmann, Ph.D. thesis, Justus, Liebig-University, Giessen, Germany), which contains the human RNA polymerase I promoter (P) and the mouse RNA polymerase I terminator (T). The thymidine nucleotide upstream of the terminator sequence (*T) represents the 3' end of the influenza viral RNA. Influenza A virus sequences are shown in bold face letters. (SEQ ID NOs: 10-19 and 28-29)

FIG. 3. Proposed reverse genetics method for generating segmented negative-sense RNA viruses. Plasmids containing the RNA polymerase I promoter a cDNA for each of the eight viral RNA segments, and the RNA polymerase I terminator are transfected into cells together with protein expression plasmids. Although infectious viruses can be generated with plasmids expressing PA, PB1, PB2, and NP, expression of all remaining structural proteins (shown in brackets) increases the efficiency of virus production depending on the virus generated.

FIG. 4. Schematic diagram of mutations introduced into the NA segment. Mutations are shown in bold (−, deletion; *, insertion). The numbers shown are nucleotide positions. (SEQ ID NOs: 20-27)

FIG. 5. Analysis of the expression of NB protein. (A) Detection of NB protein in infected MDCK cells by immunofluoresence assay. B/LeeRG, B/LeeRG-infected; WSN, A/WSN/33-infected; Control, uninfected; #1, #2, and #3, BLeeNBstop#1, BLeeNBstop#2, and BLeeNBstop#3-infected cells, respectively. (B) Detection of NB protein in virus-infected MDCK cells by immunoprecipitation assays. Radiolabeled NB proteins were immunoprecipitated with a rabbit anti-NB peptide serum and analyzed on 4-20% gradient polyacrylamide gels. #1, BLeeNBstop#1-infected; #2, BLeeNBstop#2-infected; #3, BLeeNBstop#3-infected; C, uninfected cell lysate. Molecular weight markers (kDa) are indicated.

FIG. 6. Growth curves for B/LeeRG and mutant viruses. MDCK cells were infected with virus (0.001 PFU) and incubated at 37° C. At the indicated times after infection, virus titers were determined in the supernatant. The values are means (±SD) of 3 determinations.

FIG. 7. Sequences of influenza virus B/Lee/40. (SEQ ID NOs: 1-8)

DETAILED DESCRIPTION OF THE INVENTION

Definitions

Figure 1:
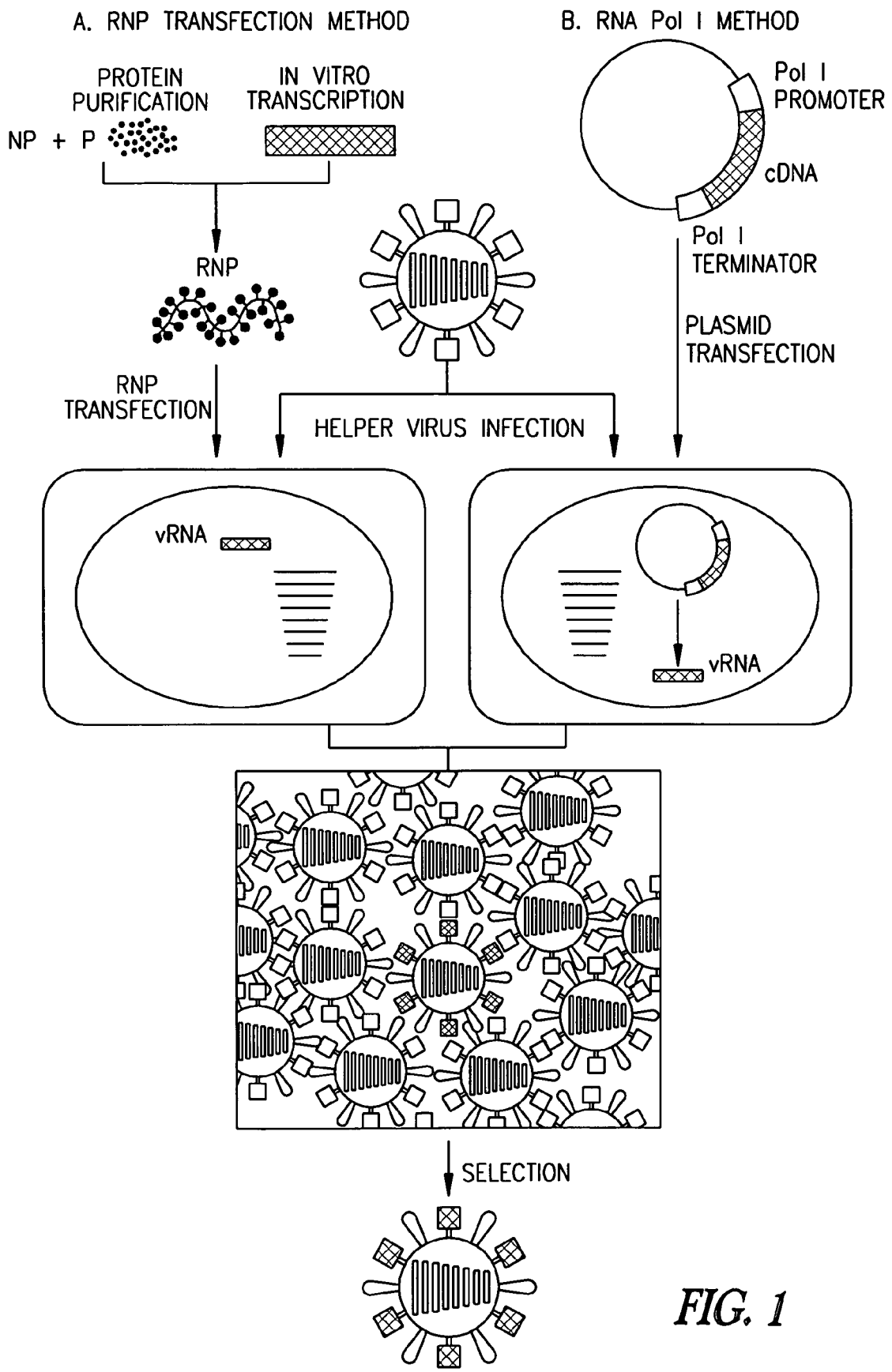
Figure 2:
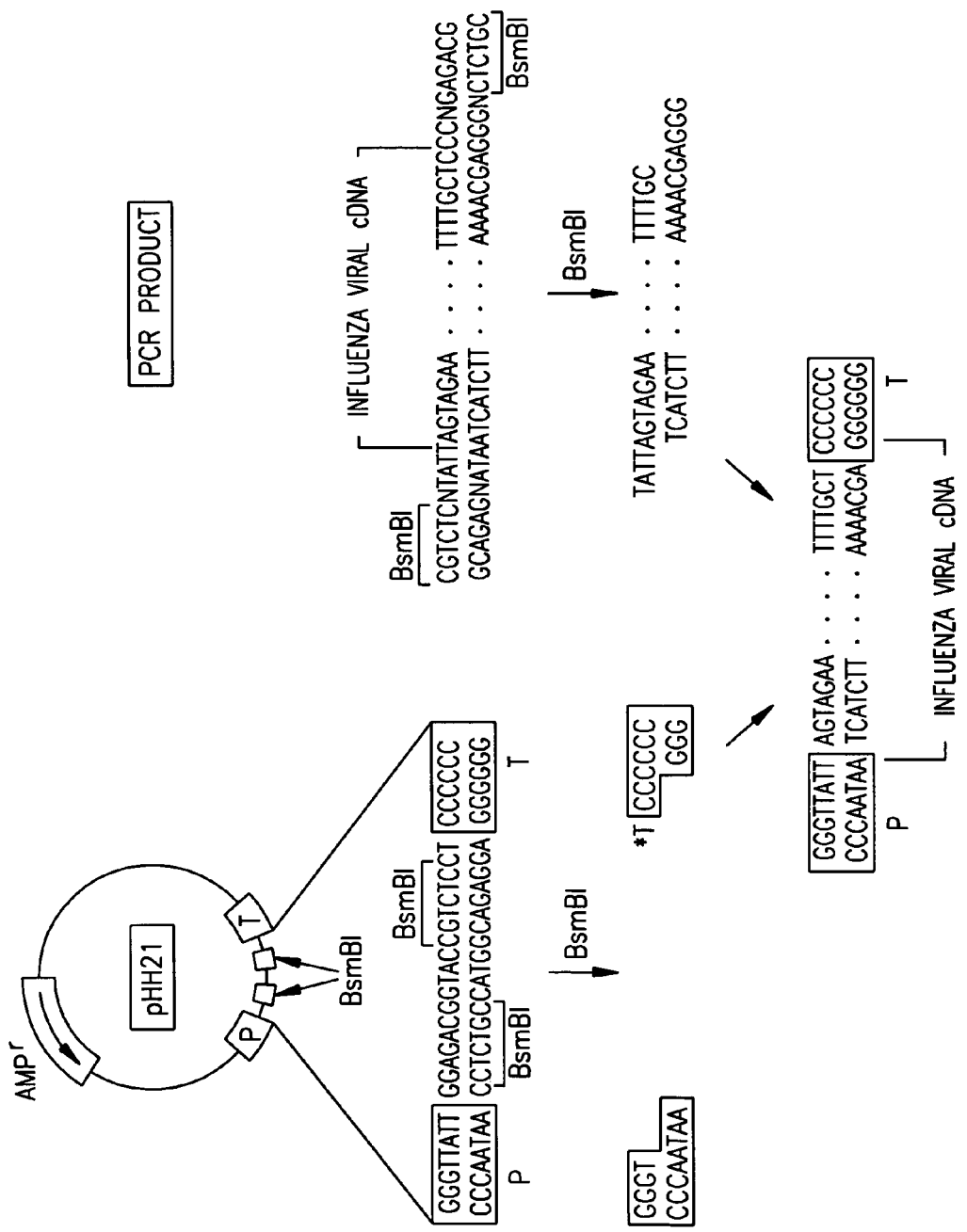

As used herein, the terms "isolated and/or purified" refer to in vitro preparation, isolation and/or purification of a vector, plasmid or virus of the invention, so that it is not associated with in vivo substances, or is substantially purified from in vitro substances. An isolated virus preparation of the invention is generally obtained by in vitro culture and propagation and is substantially free from other infectious agents. As used herein, "substantially free" means below the level of detection for a particular infectious agent using standard detection methods for that agent. A "recombinant" virus is one which has been manipulated in vitro, e.g., using recombinant DNA techniques to introduce changes to the viral genome.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome.

An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

"Low" stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C.

"Moderate" stringency conditions include hybridization in 40 to 45% formamide, 1.0 M NaCl, 1% SDS at 37° C., and a wash in 0.5× to 1×SSC at 55 to 60° C.

"Stringent" conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al., 1981; the homology alignment algorithm of Needleman and Wunsch, 1970; the search-for-similarity-method of Pearson and Lipman, 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., 1988; Higgins et al., 1989; Corpet et al., 1988; Huang et al., 1992; and Pearson et al., 1994. The ALIGN program is based on the algorithm of Myers and Miller, supra. The BLAST programs of Altschul et al., 1990, are based on the algorithm of Karlin and Altschul supra.

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching **residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (B) of 10, and the BLOSUM62 scoring matrix (see Henikoff & Henikoff, 1989). See for example the URL www.ncbi.nlm.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Orthomyxoviruses

Influenza virus

Influenza A viruses possess a genome of eight single-stranded negative-sense viral RNAs (vRNAs) that encode a total of ten proteins. The influenza virus life cycle begins with binding of the HA to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5′ cap and 3′ polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity. Similarly, influenza C virus does not have a M2 protein with ion channel activity. However, the CM1 protein is likely to have this activity. The activity of an ion channel protein may be measured by methods well-known to the art, see, e.g., Holsinger et al. (1994) and WO 01/79273.

Cell Lines and Influenza Viruses That Can Be Used in the Present Invention

According to the present invention, any cell which supports efficient replication of influenza virus can be employed in the invention, including mutant cells which express reduced or decreased levels of one or more sialic acids which are receptors for influenza virus. Viruses obtained by the methods can be made into a reassortant virus.

Preferably, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity is preferably tested in cells that are at the same passage level as those used for vaccine production. The virus is preferably purified by a process that has been shown to give consistent results, before being inactivated or attenuated for vaccine production (see, e.g., World Health Organization, 1982).

It is preferred to establish a complete characterization of the cell lines to be used, so that appropriate tests for purity of the final product can be included. Data that can be used for the characterization of a cell to be used in the present invention includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. Preferably, the passage level, or population doubling, of the host cell used is as low as possible.

It is preferred that the virus produced in the cell is highly purified prior to vaccine or gene therapy formulation. Generally, the purification procedures will result in the extensive removal of cellular DNA, other cellular components, and adventitious agents. Procedures that extensively degrade or denature DNA can also be used. See, e.g., Mizrahi, 1990.

Vaccines

A vaccine of the invention may comprise immunogenic proteins including glycoproteins of any pathogen, e.g., an immunogenic protein from one or more bacteria, viruses, yeast or fungi. Thus, in one embodiment, the influenza viruses of the invention may be vaccine vectors for influenza virus or other viral pathogens including but not limited to lentiviruses such as HIV, hepatitis B virus, hepatitis C virus, herpes viruses such as CMV or HSV or foot and mouth disease virus.

A complete virion vaccine is concentrated by ultrafiltration and then purified by zonal centrifugation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); Webster et al., 1977); or a nonionic detergent such as that commercialized under the name TRITON X100. The hemagglutinin may also be isolated after treatment of the virions with a protease such as bromelin, then purified by a method such as that described by Grand and Skehel (1972).

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

Inactivated Vaccines. Inactivated influenza virus vaccines of the invention are provided by inactivating replicated virus of the invention using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines. In general, the responses to SV and surface antigen (i.e., purified HA or NA) vaccines are similar. An experimental inactivated WV vaccine containing an NA antigen immunologically related to the epidemic virus and an unrelated HA appears to be less effective than conventional vaccines (Ogra et al., 1977). Inactivated vaccines containing both relevant surface antigens are preferred.

Live Attenuated Virus Vaccines. Live, attenuated influenza virus vaccines, can also be used for preventing or treating influenza virus infection, according to known method steps. Attenuation is preferably achieved in a single step by transfer of attenuated genes from an attenuated donor virus to a replicated isolate or reassorted virus according to known methods (see, e.g., Murphy, 1993). Since resistance to influenza A virus is mediated by the development of an immune response to the HA and NA glycoproteins, the genes coding for these surface antigens must come from the reassorted viruses or high growth clinical isolates. The attenuated genes are derived from the attenuated parent. In this approach, genes that confer attenuation preferably do not code for the HA and NA glycoproteins. Otherwise, these genes could not be transferred to reassortants bearing the surface antigens of the clinical virus isolate.

Many donor viruses have been evaluated for their ability to reproducibly attenuate influenza viruses. As a non-limiting example, the A/Ann Arbor(AA)/6/60 (H2N2) cold adapted (ca) donor virus can be used for attenuated vaccine production (see, e.g., Edwards, 1994; Murphy, 1993). Additionally, live, attenuated reassortant virus vaccines can be generated by mating the ca donor virus with a virulent replicated virus of the invention. Reassortant progeny are then selected at 25° C., (restrictive for replication of virulent virus), in the presence of an H2N2 antiserum, which inhibits replication of the viruses bearing the surface antigens of the attenuated A/AA/6/60 (H2N2) ca donor virus.

A large series of H1N1 and H3N2 reassortants have been evaluated in humans and found to be satisfactorily: (a) infectious, (b) attenuated for seronegative children and immunologically primed adults, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible adults and children.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene (Subbarao et al., 1993). Thus, new donor viruses can also be generated bearing attenuating mutations introduced by site-directed mutagenesis, and such new donor viruses can be used in the reduction of live attenuated reassortants H1N1 and H3N2 vaccine candidates in a manner analogous to that described above for the A/AA/6/60 ca donor virus. Similarly, other known and suitable attenuated donor strains can be reasserted with influenza virus of the invention to obtain attenuated vaccines suitable for use in the vaccination of mammals (Ewami et al., 1990; Muster et al., 1991; Subbarao et al., 1993).

It is preferred that such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking infectivity to the degree that the vaccine causes minimal change of inducing a serious pathogenic condition in the vaccinated mammal.

The virus can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) are not present in the attenuated viruses. See, e.g., Robertson et al., 1988; Kilbourne, 1969; Aymard-Henry et al., 1985; Robertson et al., 1992.

Pharmaceutical Compositions

Pharmaceutical compositions of the present invention, suitable for inoculation or for parenteral or oral administration, comprise attenuated or inactivated influenza viruses, optionally further comprising sterile aqueous or non-aqueous solutions, suspensions, and emulsions. The compositions can further comprise auxiliary agents or excipients, as known in the art. See, e.g., Berkow et al., 1987; Goodman et al., 1990; *Avery's Drug Treatment*, 1987; Osol, 1980; Katzung, 1992. The composition of the invention is generally presented in the form of individual doses (unit doses).

Conventional vaccines generally contain about 0.1 to 200 μg, preferably 10 to 15 μg, of hemagglutinin from each of the strains entering into their composition. The vaccine forming the main constituent of the vaccine composition of the invention may comprise a virus of type A, B or C, or any combination thereof, for example, at least two of the three types, at least two of different subtypes, at least two of the same type, at least two of the same subtype, or a different isolate(s) or reassortant(s). Human influenza virus type A includes H1N1, H2N2 and H3N2 subtypes.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Berkow et al., 1992; Goodman et al., 1990; Avery's, 1987; Osol, 1980; and Katzung, 1992.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized. Examples of materials suitable for use in vaccine compositions are provided in Osol (1980).

Heterogeneity in a vaccine may be provided by mixing replicated influenza viruses for at least two influenza virus strains, such as 2-50 strains or any range or value therein. Influenza A or B virus strains having a modern antigenic composition are preferred. According to the present invention, vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir. See, e.g., Katzung (1992), and the references cited therein on pages 798-800 and 680-681, respectively.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines, are provided before any symptom of a pathogen infection becomes manifest. The prophylactic administration of the composition serves to prevent or attenuate any subsequent infection. When provided prophylactically, the gene therapy compositions of the invention, are provided before any symptom of a disease becomes manifest. The prophylactic administration of the composition serves to prevent or attenuate one or more symptoms associated with the disease.

When provided therapeutically, an attenuated or inactivated viral vaccine is provided upon the detection of a symptom of actual infection. The therapeutic administration of the compound(s) serves to attenuate any actual infection. See, e.g., Berkow et al., 1992; Goodman et al., 1990; Avery, 1987; and Katzung, 1992. When provided therapeutically, a gene therapy composition is provided upon the detection of a symptom or indication of the disease. The therapeutic administration of the compound(s) serves to attenuate a symptom or indication of that disease.

Thus, an attenuated or inactivated vaccine composition of the present invention may thus be provided either before the onset of infection (so as to prevent or attenuate an anticipated infection) or after the initiation of an actual infection. Similarly, for gene therapy, the composition may be provided before any symptom of a disorder or disease is manifested or after one or more symptoms are detected.

A composition is said to be "pharmacologically acceptable" if its administration can be tolerated by a recipient patient. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of patients. Protection may be limited to mitigating the severity or rapidity of onset of symptoms of the influenza virus infection.

Pharmaceutical Administration

A composition of the present invention may confer resistance to one or more pathogens, e.g., one or more influenza virus strains, by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a symptom or condition of the disease, or in the total or partial immunity of the individual to the disease. As used herein, a gene therapy composition is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular or subcutaneous application. See, e.g., Berkow et al., 1992; Goodman et al., 1990; Avery, 1987; and Katzung, 1992.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent preferred dose ranges. However, the most preferred dosage will be tailored to the individual subject, as is understood and determinable by one of skill in the art. See, e.g., Berkow et al., 1992; Goodman et al., 1990; Avery's, 1987; Ebadi, 1985; and Katsung, 1992.

The dosage of an attenuated virus vaccine for a mammalian (e.g., human) or avian adult organism can be from about $10^3$-$10^7$ plaque forming units (PFU)/kg, or any range or value therein. The dose of inactivated vaccine can range from about 0.1 to 200, e.g., 50 μg of hemagglutinin protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 1-50 μg or any range or value therein, or the amount recommended by the U.S. Public Heath Service (PHS), which is usually 15 μg, per component for older children. 3 years of age, and 7.5 μg per component for older children<3 years of age. The quantity of NA can also be standardized, however, this glycoprotein can be labile during the processor purification and storage (Kendal et al., 1980; Kerr et al., 1975). Each 0.5-ml dose of vaccine preferably contains approximately 1-50 billion virus particles, and preferably 10 billion particles.

The invention will be further described by the following non-limiting examples.

EXAMPLE 1

Materials and Methods

Cells and viruses. 293T human embryonic kidney cells and Madin-Darby canine kidney cells (MDCK) were maintained in Dulbecco's modified Eagle medium (DMEM) supplemented with 10% fetal calf serum and in modified Eagle's medium (MEM) containing 5% newborn calf serum, respectively. All cells were maintained at 37° C. in 5% $CO_2$. Influenza viruses A/WSN/33 (H1N1) and A/PR/8/34 (H1N1) were propagated in 10-day-old eggs.

Construction of plasmids. To generate RNA polymerase I constructs, cloned cDNAs derived from A/WSN/33 or A/PR/8/34 viral RNA were introduced between the promoter and terminator sequences of RNA polymerase I. Briefly, the cloned cDNAs were amplified by PCR with primers containing BsmBI sites, digested with BsmBI, and cloned into the BsmBI sites of the pHH21 vector which contains the human RNA polymerase I promoter and the mouse RNA polymerase I terminator, separated by BsmBI sites (FIG. 2). The PB2, PB1, PA, HA, NP, NA, M, and NS genes of the A/WSN/33 strain were PCR-amplified by use of the following plasmids: pSCWPB2, pGW-PB1, and pSCWPA (all obtained from Dr. Debi Nayak at the University of California Los Angeles), and pWH17, pWNP152, pT3WNA15 (Castrucci et al., 1992), pGT3WM, and pWNS1, respectively. The PB1 gene of influenza A/PR/8/34 virus was amplified by using pcDNA774 (PB1) (Perez et al., 1998) as a template. To ensure that the genes were free of unwanted mutations, PCR-derived fragments were sequences with an autosequencer (Applied Biosystem Inc., CA, USA) according to the protocol recommended by the manufacturer. The cDNAs encoding the HA, NP, NA, and M1 genes of A/WSN/33 virus were cloned as described (Huddleston et al., 1982) and subcloned into the eukaryotic expression vector pCAGGS/MCS (controlled by the chicken β-actin promoter) (Niwa et al., 1991), resulting in pEWSN-HA, pCAGGS-WSN-NP0-14, pCAGGS-WNA15, and pCAGGS-WSN-M1-2/1, respectively. The M2 and NS2 genes from the A/PR/8/34 virus were amplified by PCR and cloned into pCAGGS/MCS, yielding pEP24c and pCA-NS2. Finally, pcDNA774(PB1), pcDNA762(PB2), and pcDNA787(PA) were used to express the PB2, PB1, and PA proteins under control of the cytomegalovirus promoter (Perez et al., 1998).

Generation of infectious influenza particles. 293T cells ($1\times10^6$) were transfected with a maximum of 17 plasmids in different amounts with use of Trans IT LT-1 (Panvera, Madison, Wis.) according to the manufacturer's instructions. Briefly, DNA and transfection reagent were mixed (2 μl Trans IT-LT-1 per μg of DNA), incubated at room temperature for 45 minutes and added to the cells. Six hours later, the DNA-transfection reagent mixture was replaced by Opti-MEM (Gibco/BRL, Gaithersburg, Md.) containing 0.3% bovine serum albumin and 0.01% fetal calf serum. At different times after transfection, viruses were harvested from the supernatant and titrated on MDCK cells. Since helper virus was not required by this procedure, the recovered transfectant viruses were analyzed without plaque purification.

Determination of the percentage of plasmid-transfected cells producing viruses. Twenty-four hours after transfection, 293T cells were dispersed with 0.02% EDTA into single cells. The cell suspension was then diluted 10-fold and transferred to confluent monolayers of MDCK cells in 24-well plates. Viruses were detected by the hemagglutination assay.

Immunostaining assay. Nine hours after infection with influenza virus, cells were washed twice with phosphatebuffered saline (PBS) and fixed with 3.7% paraformaldehyde (in PBS) for 20 minutes at room temperature. Next, they were treated with 0.1% Triton X-100 and processed as described by Neumann et al. (1997).

fection of 293T cells, $7 \times 10^3$ pfu of virus per ml was found in the supernatant (Experiment 1, Table 1), demonstrating for the first time the capacity of reverse genetics to produce influenza A virus entirely from plasmids.

TABLE 1

Plasmid sets used to produce influenza virus from cloned cDNA*

| | Experiment | | | | | | | |
|---|---|---|---|---|---|---|---|---|
| | 1 | 2 | 3 | 4 | 5 | 6 | 7 | 8 |
| RNA polymerase I plasmids for:[†] | | | | | | | | |
| PB1 | + | + | − | − | − | − | − | − |
| PR8-PB1 | − | − | + | + | + | + | + | + |
| PB2 | + | + | + | + | + | + | + | + |
| PA | + | + | + | + | + | + | + | + |
| HA | + | + | + | + | + | + | + | + |
| NP | + | + | + | + | + | + | + | + |
| NA | + | + | + | + | + | + | + | + |
| M | + | + | + | + | + | + | + | + |
| NS | + | + | + | + | + | + | + | + |
| Protein expression plasmids for: | | | | | | | | |
| PB1 | + | + | + | + | − | + | + | + |
| PB2 | + | + | + | + | + | − | + | + |
| PA | + | + | + | + | + | + | − | + |
| NP | + | + | + | + | + | + | + | − |
| HA | − | + | − | + | + | + | + | + |
| NA | − | + | − | + | + | + | + | + |
| M1 | − | + | − | + | + | + | + | + |
| M2 | − | + | − | + | + | + | + | + |
| NS2 | − | + | − | + | + | + | + | + |
| Virus titer (pfu/ml) | $7 \times 10^3$ | $7 \times 10^3$ | $1 \times 10^3$ | $3 \times 10^4$ | 0 | 0 | 0 | 0 |

*293T cells were transfected with the indicated plasmids. Twenty-four (Experiments 1 and 2) or forty-eight hours (Experiments 3-8) later, the virus titer in the supernatant was determined in MDCK cells.
[†]Unless otherwise indicated, plasmids were constructed with cDNAs representing the RNAs of A/WSN/33 virus.

Results

Figure 3:
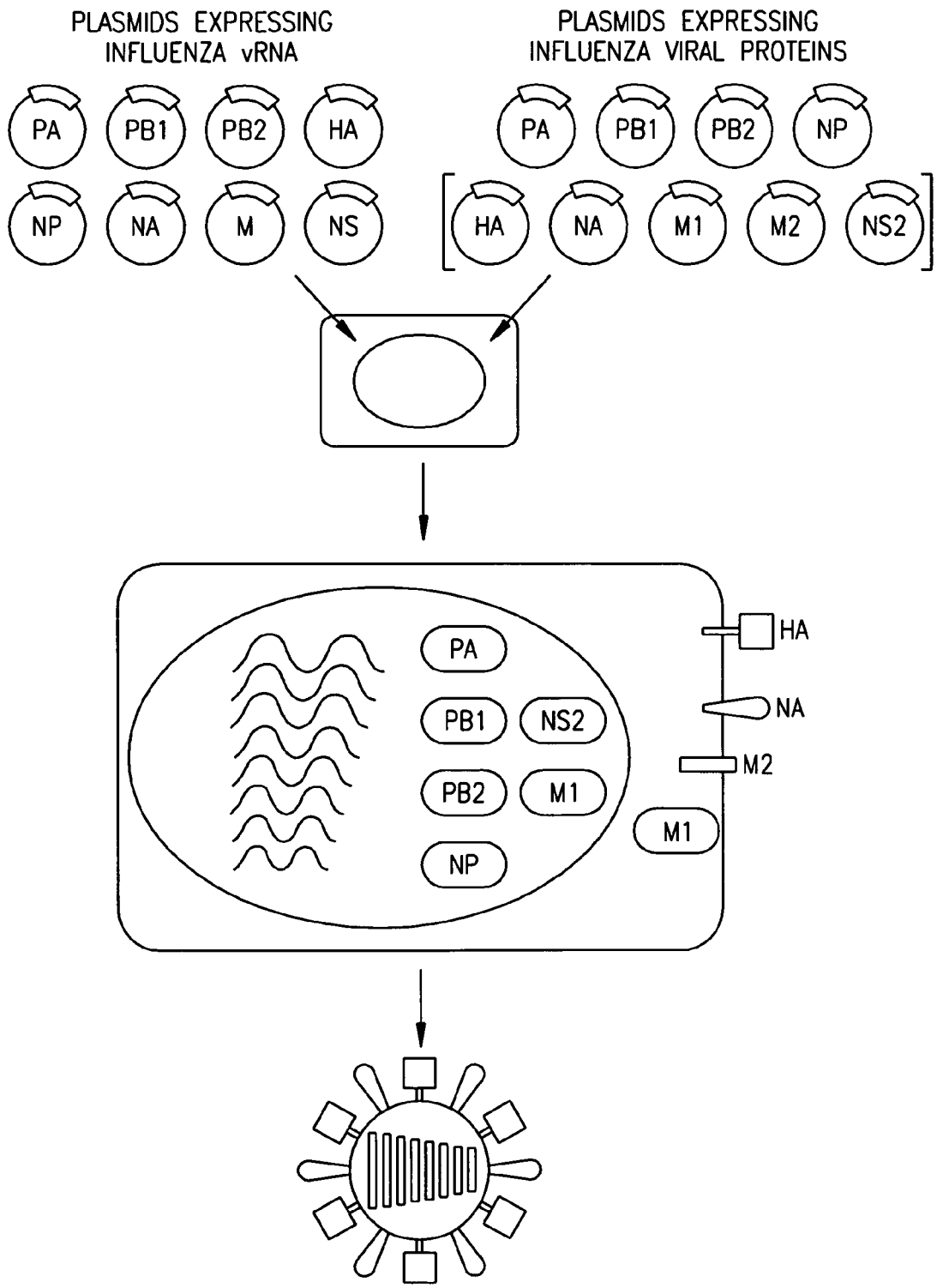

Generation of infectious virus by plasmid-driven expression of viral RNA segments, three polymerase subunits and NP protein. Although transfection of cells with a mixture of RNPs extracted from purified virions results in infectious influenza particles, this strategy is not likely to be efficient when used with eight different in vitro generated RNPs. To produce infectious influenza viruses entirely from cDNAs, eight viral RNPs were generated in vivo. Thus, plasmids were prepared that contain cDNAs for the full-length viral RNAs of the A/WSN/33 virus, flanked by the human RNA polymerase I promoter and the mouse RNA polymerase I terminator. In principle, transfection of these eight plasmids into eukaryotic cells should result in the synthesis of all eight influenza vRNAs. The PB2, PB1, PA and NP proteins, generated by cotransfection of protein expression plasmids, should then assemble the vRNAs into functional vRNPs that are replicated and transcribed, ultimately forming infectious influenza viruses (FIG. 3). $1 \times 10^6$ 293T cells were transfected with protein expression plasmids (1 µg of pcDNA762(PB2), 1 µg of pcDNA774(PB1), 0.1 µg of pcDNA787(PA), and 1 µg of pCAGGS-WSN-NP0/14) and 1 µg of each of the following RNA polymerase I plasmids (pPolI-WSN-PB2, pPolI-WSN-PB1, pPolI-WSN-PA, pPolI-WSN-HA, pPolI-WSN-NP, pPolI-WSN-NA, pPolI-WSN-M, and pPolI-WSN-NS). The decision to use a reduced amount of pcDNA787(PA) was based on previous observations (Mena et al., 1996), and data on the optimal conditions for generation of virus-like particles (VLPs) (data not shown). Twenty-four hours after trans- Efficiency of influenza virus production with coexpression of all viral structural proteins. Although expression of the viral NP and polymerase proteins is sufficient for the plasmid-driven generation of influenza viruses, it was possible that the efficiency could be improved. In previous studies, the expression of all influenza virus structural proteins (PB2, PB1, PA, HA, NP, NA, M1, M2, and NS2) resulted in VLPs that contained an artificial vRNA encoding a reporter chloramphenicol-acetyltransferase gene (Mena et al., 1996). Thus, the availability of the entire complement of structural proteins, instead of only those required for viral RNA replication and transcription, might improve the efficiency of virus production. To this end, 293T cells were transfected with optimal amounts of viral protein expression plasmids (as judged by VLP production; unpublished data): 1 µg of pcDNA762 (PB2) and pcDNA774(PB1); 0.1 µg of pcDNA787(PA); 1 µg of pEWSN-HA, pCAGGS-WSN-NP0/14, and pCAGGS-WNA15; 2 µg of pCAGGS-WSN-M1-2/1; 0.3 µg of pCA-NS2; and 0.03 µg of pEP24c (for M2), together with 1 µg of each RNA polymerase I plasmid (Experiment 2, Table 1). A second set of cells was transfected with the same set of RNA polymerase I plasmids, with the exception of the PB1 gene, for which pPolI-PR/8/34-PB1 was substituted in an effort to generate a reassortant virus, together with plasmids expressing only PA, PB1, PB2, and NP (Experiment 3, Table 1) or those expressing all the influenza structural proteins (Experiment 4, Table 1). Yields of WSN virus did not appreciably differ at 24 hours (Experiments 1 and 2, Table 1) or at 36 hours (data not shown) post-transfection. However, more than a 10-fold increase in yields of the virus with PR/8/34-PB1 was found when all the influenza viral structural proteins were provided (Experiments 3 and 4, Table 1). Negative controls, which lacked one of the plasmids for the expression of PA, PB1, PB2, of NP proteins, did not yield any virus (Experiments 5-8, Table 1). Thus, depending on the virus generated, expression of all influenza A virus structural proteins appreciably improved the efficiency of the reverse genetics method.

Next, the kinetics of virus production after transfection of cells was determined using the set of plasmids used to generate a virus with the A/PR/8/34-PB1 gene. In two of three experiments, virus was first detected at 24 hours after transfection. The titer measured at that time, >$10^3$ pfu/ml, had increased to >$10^6$ pfu/ml by 48 hours after transfection (Table 2). To estimate the percentage of plasmid-transfected cells that were producing viruses, 293T cells were treated with EDTA (0.02%) at 24 hours after transfection to disperse the cells, and then performed limiting dilution studies. In this experiment, no free virus was found in the culture supernatant at this time point. The results indicated that 1 in $10^{3.3}$ cells was generating infectious virus particles.

TABLE 2

Kinetics of virus production after plasmid transfection into 293T cells*

| Hours after plasmid transfection | Virus titers in culture supernatant (pfu/ml) Experiment | | |
|---|---|---|---|
| | 1 | 2 | 3 |
| 6 | 0 | ND | ND |
| 12 | 0 | ND | 0 |
| 18 | 0 | ND | 0 |
| 24 | 0 | $2 \times 10^3$ | $6 \times 10^3$ |
| 30 | ND | $5 \times 10^4$ | $9 \times 10^4$ |
| 36 | $6 \times 10^2$ | >$1 \times 10^5$ | $7 \times 10^5$ |
| 42 | ND | >$1 \times 10^6$ | $5 \times 10^6$ |
| 48 | $8 \times 10^4$ | >$1 \times 10^6$ | $1 \times 10^7$ |

*293T cells were transfected with eight RNA polymerase I plasmids encoding A/WSN/33 virus genes with the exception of PB1 gene, which is derived from A/PR/8/34 virus, and nine protein expression plasmids as described in the text. At different time points, we titrated virus in the culture supernatant in MDCK cells.
ND = not done.

Recovery of influenza virus containing the FLAG epitope in the NA protein. To verify that the new reverse genetics system allowed the introduction of mutations into the genome of influenza A viruses, a virus containing a FLAG epitope (Castrucci et al., 1992) in the NA protein was generated. 293T cells were transfected with an RNA polymerase I plasmid (pPolI-WSN-NA/FL79) that contained a cDNA encoding both the NA protein and a FLAG epitope at the bottom of the protein's head, together with the required RNA polymerase I and protein expression plasmids. To confirm that the recovered virus (PR8-WSN-FL79) did in fact express the NA-FLAG protein, immunostaining assays of cells infected with PR8-WSN-FL79 or A/WSN/33 wild-type virus was performed. A monoclonal antibody to the FLAG epitope detected cells infected with PR8-WSN-FL79, but not those infected with wild-type virus. Recovery of the PR8-WSN-FL79 virus was as efficient as that for the untagged wild-type virus (data not shown). These results indicate that the new reverse genetics system allows one to introduce mutations into the influenza A virus genome.

Generation of infectious influenza virus containing mutations in the PA gene. To produce viruses possessing mutations in the PA gene, two silent mutations were introduced creating new recognition sequences for restriction endonucleases (Bsp120I at position 846 and PvuII at position 1284 of the mRNA). Previously, it was not possible to modify this gene by reverse genetics, because of the lack of a reliable selection system. Transfectant viruses, PA-T846C and PA-A1284 were recovered. The recovered transfectant viruses were biologically cloned by two consecutive limiting dilutions. To verify that the recovered viruses were indeed transfectants with mutations in the PA gene, cDNA for the PA gene was obtained by reverse transcriptase-PCR. PA-T846C and PA-A1284C viruses had the expected mutations within the PA gene, as demonstrated by the presence of the newly introduced restriction sites. PCR of the same viral samples and primers without the reverse transcription step failed to produce any products (data not shown), indicating that the PA cDNA was indeed originated from vRNA instead of the plasmid used to generate the viruses. These results illustrate how viruses with mutated genes can be produced and recovered without the use of helper viruses.

Discussion

The reverse genetics systems described herein allows one to efficiently produce influenza A viruses entirely from cloned cDNAs. Bridgen and Elliott (1996) also used reverse genetics to generate a Bunyamwera virus (Bunyaviridae family), but it contains only three segments of negative-sense RNA, and the efficiency of its production was low, $10^2$ pfu/$10^7$ cells. Although the virus yields differed among the experiments, consistently >$10^3$ pfu/$10^6$ cells was observed for influenza virus, which contains eight segments. There are several explanations for the high efficiency of the reverse genetics system described hereinabove. Instead of producing RNPs in vitro (Luytjes et al., 1989), RNPs were generated in vivo through intracellular synthesis of vRNAs using RNA polymerase I and through plasmid-driven expression of the viral polymerase proteins and NP. Also, the use of 293T cells, which are readily transfected with plasmids (Goto et al., 1997), ensured that a large population of cells received all of the plasmids needed for virus production. In addition, the large number of transcripts produced by RNA polymerase I, which is among the most abundantly expressed enzymes in growing cells, likely contributed to the overall efficiency of the system. These features led to a correspondingly abundant number of vRNA transcripts and adequate amounts of viral protein for encapsidation of vRNA, formation of RNPs in the nucleus, and export of these complexes to the cell membrane, where new viruses are assembled and released.

Previously established reverse genetics systems (Enami et al., 1990; Neumann et al., 1994; Luytjes et al., 1989; Pleschka et al., 1996) require helper-virus infection and therefore selection methods that permit a small number of transfectants to be retrieved from a vast number of helper viruses. Such strategies have been employed to generate influenza viruses that possess one of the following cDNA-derived genes: PB2 (Subbarao et al., 1993), HA (Enami et al., 1991: Horimoto et al., 1994), NP (Li et al., 1995), NA (Enami et al., 1990), M (Castrucci et al., 1995; Yasuda et al., 1994), and NS (Enami et al., 1991). Most of the selection methods, except for those applicable to the HA and NA genes, rely on growth temperature, host range restriction, or drug sensitivity, thus limiting the utility of reverse genetics for functional analysis of the gene products. Even with the HA and NA genes, for which reliable antibody-driven selection systems are available, it is difficult to produce viruses with prominent growth defects. In contrast, the reverse genetics system described herein does not require helper virus and permits one to generate transfectants with mutations in any gene segment or with severe growth defects. This advantage is demonstrated in FIG. 5, which the recovery of transfectant viruses with a mutated PA gene. Having the technology to introduce any viable mutation into the influenza A virus genome will enable investigators to address a number of long-standing issues, such as the nature of regulatory sequences in nontranslated regions of the viral genome, structure-function relationships of viral proteins, and the molecular basis of host-range restriction and viral pathogenicity.

Although inactivated influenza vaccines are available, their efficacy is suboptimal due partly to their limited ability to elicit local IgA and cytotoxic T cell responses. Clinical trials of cold-adapted live influenza vaccines now underway suggest that such vaccines are optimally attenuated, so that they will not cause influenza symptoms, but will still induce protective immunity (reviewed in Keitel & Piedra, 1998). However, preliminary results indicate that these live virus vaccines will not be significantly more effective than the best inactivated vaccine (reviewed in Keitel. & Piedra, 1998), leaving room for further improvement. One possibility would be to modify a cold-adapted vaccine with the reverse genetics system described above. Alternatively, one could start from scratch by using reverse genetics to produce a "master" influenza A strain with multiple attenuating mutations in the genes that encode internal proteins. The most intriguing application of the reverse genetics system described herein may lie in the rapid production of attenuated live-virus vaccines in cases of suspected pandemics involving new HA or NA subtypes of influenza virus.

This new reverse genetics system will likely enhance the use of influenza viruses as vaccine vectors. The viruses can be engineered to express foreign proteins or immunogenic epitopes in addition to the influenza viral proteins. One could, for example, generate viruses with foreign proteins as a ninth segment (Enami et al., 1991) and use them as live vaccines. Not only do influenza viruses stimulate strong cell-mediated and humoral immune responses, but they also afford a wide array of virion surface HA and NA proteins (e.g., 15 HA and 9 NA subtypes and their epidemic variants), allowing repeated immunization of the same target population.

Influenza VLPs possessing an artificial vRNA encoding a reporter gene have been produced by expressing viral structural proteins and vRNA with the vaccinia-T7 polymerase system (Mena et al., 1996). Using reverse genetics, one can now generate VLPs containing vRNAs that encode proteins required for vRNA transcription and replication (i.e., PA, PB1, PB2, and NP), as well as vRNAs encoding proteins of interest. Such VLPs could be useful gene delivery vehicles. Importantly, their lack of genes encoding viral structural proteins would ensure that infectious viruses will not be produced after VLP-gene therapy. Since the influenza virus genome is not integrated into host chromosome, the VLP system would be suitable for gene therapy in situations requiring only short-term transduction of cells (e.g., for cancer treatment). In contrast to adenovirus vectors (Kovesdi et al., 1997), influenza VLPs could contain both HA and NA variants, allowing repeated treatment of target populations.

The family Orthomyxoviridae comprises influenza A, B, and C viruses, as well as the recently classified Thogotovirus. The strategy for generating infectious influenza A viruses entirely from cloned cDNAs described herein would apply to any orthomyxovirus, and perhaps to other segmented negative-sense RNA viruses as well (e.g., Bunyaviridae, Arenaviridae). The ability to manipulate the viral genome without technical limitations has profound implications for the study of viral life cycles and their regulation, the function of viral proteins and the molecular mechanisms of viral pathogenicity.

EXAMPLE 2

Materials and Methods

Cells, viruses, and antibodies. 293T human embryonic kidney cells and Madin-Darby canine kidney (MDCK) cells were maintained in DMEM supplemented with 10% fetal calf serum and in MEM containing 5% newborn calf serum, respectively. The 293T cell line is a derivative of the 293 line, into which the gene for the simian virus 40 T antigen was inserted (DuBridge et al., 1987). All cells were maintained at 37° C. in 5% $CO_2$. B/Lee/40 and its mutant viruses were propagated in 10-day-old embryonated chicken eggs. The viruses were purified from allantoic fluid by differential centrifugation and sedimentation through a 10-50% sucrose gradient. An anti-NB rabbit serum was generated against synthesized peptide NKRDDISTPRAGVD (SEQ ID NO:9; amino acid residues 70-83 of NB protein) coupled to keyhole limpet hemocyanin.

Construction of plasmids. The cDNAs of B/Lee/40 viruses were synthesized by reverse transcription of viral RNA with an oligonucleotide complementary to the conserved 3' end of the viral RNA. The cDNA was amplified by PCR with gene-specific oligonucleotide primers containing Bsm BI sites, and PCR products were cloned into the pT7Blueblunt vector (Novagen, Madison, Wis.). After digestion with Bsm BI, the fragment was cloned into the Bsm BI sites of a plasmid vector, which contains the human RNA polymerase I promoter and the mouse RNA polymerase I terminator, separated by Bsm BI sites. These plasmids for the expression of vRNA are referred to as "PolI" constructs. The cDNAs encoding the PB2, PB1, PA, and NP genes of B/Lee/40 virus were cloned into the eukaryotic expression vector pCAGGS/MCS (controlled by the chicken β-actin promoter) (Kobasa et al., 1997; Niwa et al., 1991), resulting in pCABLeePB2, pCABLeePB1, pCABLeePA, and pCABLeeNP, which express the PB2, PB1, PA, and NP proteins, respectively.

The NB knockout mutants were constructed as follows. Mutated NA genes (see FIG. 4) were amplified by PCR from the PolI construct containing B/Lee/40 NA gene and then digested with Bsm BI. The Bsm BI-digested fragment was cloned into the Bsm BI sites of the PolI plasmid. The resulting constructs were designated pPolBLeeNBstop#1, pPolBLeeNBstop#2, and pPolBLeeNBstop#3. All of the constructs were sequenced to ensure that unwanted mutations were not present.

Plasmid-based reverse genetics. Transfectant viruses were generated as reported earlier (Example 1). Briefly, 12 plasmids (eight PolI constructs for eight RNA segments and four protein-expression constructs for polymerase proteins and NP) were mixed with transfection reagent (Trans IT LT-1 [Panvera, Madison, Wis.]), incubated at room temperature for 10 minutes, and added to $1 \times 10^6$ 293T cells cultured in Opti-MEM (Invitrogen) containing 0.3% BSA. Forty-eight hours later, viruses in the supernatant were collected and amplified in MDCK cells for the production of stock viruses.

Indirect immunofluoresence assay. MDCK cells were infected with viruses at a multiplicity of infection (MOI) of 1 to about 2 plaque-forming units (PFU) per cell. After 8 hours of infection, cells were fixed with 3% formaldehyde solution and permeated with 0.1% Triton X-100. Antigens were detected with rabbit anti-NB peptide rabbit serum as a primary antibody and FITC-conjugated anti-rabbit IgG as a secondary antibody.

Immunoprecipitation. Influenza B virus-infected MDCK cells (MOI of 5 PFU/cell) were labeled with a mixture of [$^{35}$S]Met and [$^{35}$S]Cys (50 µCi/ml each) (Tran $^{35}$S-label; ICN Biochemicals) at 7 hours postinfection for 2 hours. The radiolabeled cells were lysed in RIPA buffer containing 10 mM Tris-HCl (pH 7.5), 100 mM NaCl, 1 mM EDTA, and 0.5% Triton X-100 and then centrifuged. The anti-NB rabbit serum was added to the supernatant and incubated overnight at 4° C. Protein A-Sepharose beads were then added and incubated for 1 hour at room temperature. The immune complexes were washed and separated on 4-20% gradient polyacrylamide gels (ISC BioExpress, Kaysville, Utah). The gels were dried and examined by autoradiography.

Replicative properties of transfectant viruses. MDCK cells were infected with viruses at MOI of 0.001 PFU per cells, overlaid with MEM medium containing 0.5 µg of trypsin per ml, and incubated at 37° C. Supernatants were assayed at different times for infectious virus in plaque assays on MDCK cells.

Experimental infection. Five-week-old female BALB/c mice, anesthetized with methoxyflurane, were infected intranasally with 50 µl of virus. The dose lethal for 50% of mice ($MLD_{50}$) was determined as previously described in Gao et al. (1999). The replicative capacity of virus was determined by intranasally infecting mice ($1.0 \times 10^4$ PFU) and determining virus titers in organs at 3 days postinfection, as described by Bilsel et al. (1993).

Results

Generation of B/Lee/40 virus by reverse genetics. As a first step in determining the role(s) of NB protein in virus replication, B/Lee/40 (B/Lee) virus was generated entirely from cloned cDNA, using plasmid-based reverse genetics (Neumann et al., 1999). The plasmids contained cDNAs encoding all eight segments of B/Lee virus, flanked by the human RNA polymerase I promoter and the mouse RNA polymerase I terminator. Then 293T cells were transfected with four plasmids expressing PA, PB1, PB2 and NP proteins of B/Lee virus and eight plasmids that directed the production of 8 viral RNA segments of B/Lee virus. Forty-eight hours after transfection, the virus, designated B/LeeRG, was recovered from the supernatant of 293T cells ($10^{3.5}$ 50% tissue culture infectious dose, $TCID_{50}$).

NB protein-knockout viruses are viable. Using this reverse genetics system, mutant viruses that did not express the NB protein were generated. Three mutant PolI constructs designated pPolBLeeNBstop#1, pPolBLeeNBstop#2, and pPolBLeeNBstop#3 were prepared (FIG. 4). In all mutant constructs, the initiation codon of the NB protein was converted from ATG to GCG (Met to Ala), and the codon at amino acid position 41 of NB protein was changed from AAA to TAA (stop codon). pPolBLeeNBstop#2 has a single nucleotide deletion downstream of the mutated initiation codon, which was expected to alter the reading frame of NB protein. pPolBLeeNBstop#3 has a nucleotide insertion downstream of the mutated initiation codon, which also was expected to alter the reading frame of the NB protein. At 48 hours after transfection of 293T cells with each mutant NA PolI plasmid, together with seven other PolI plasmids and four protein expression plasmids, BLeeNBstop#1, BLeeNBstop#2, and BLeeNBstop#3 were recovered from the supernatant ($10^{3.5}$ $TCID_{50}$), indicating that all viruses lacking the NB protein were generated with an efficiency equivalent to that for the wild-type B/Lee virus. The transfectant viruses present in the supernatant were grown in MDCK cells and used as stock viruses. Sequencing of the NA gene of each stock virus confirmed the stability of the desired mutations and ruled out the introduction of additional mutations.

Figure 5A:
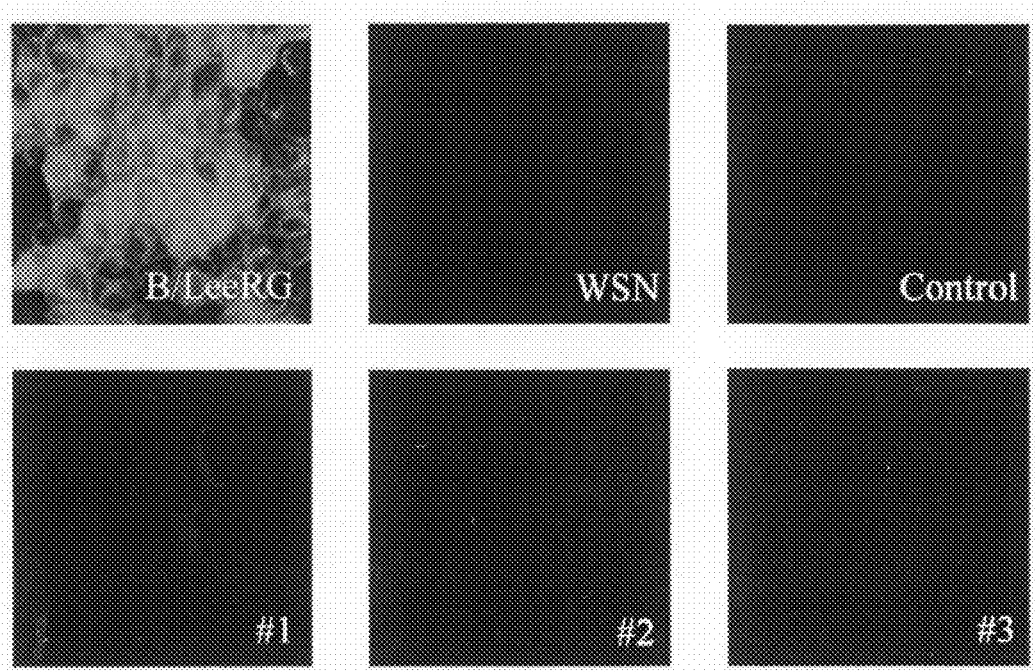
Figure 5B:
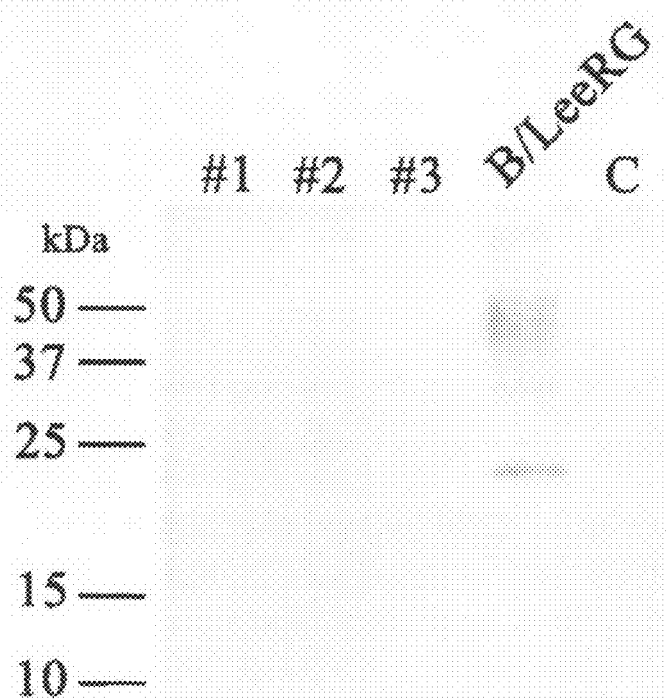

To confirm that the three mutant viruses did not express NB protein, as intended, indirect immunofluoresence assays and immunoprecipitation assays were performed using virus-infected MDCK cells (FIG. 5). None of the mutants were positive, in contrast to the B/LeeRG virus, which expressed NB. In immunoprecipitation studies, NB protein was identified as a 1.8-kDa protein (high-mannose form) and as about 30- to 50-kDa proteins (heterogeneous form) in agreement with the previously reported results (Williams et al., 1986; Williams et al., 1988). Several cells infected with BLeeNBstop#1 virus showed faint, diffuse cytoplasmic staining in the immunofluoresence assays, which might indicate the production of a short NB peptide produced by alternative initiation and read through of the stop codon introduced. Thus, all three mutant viruses were viable and did not express the full-length NB protein.

Figure 6:
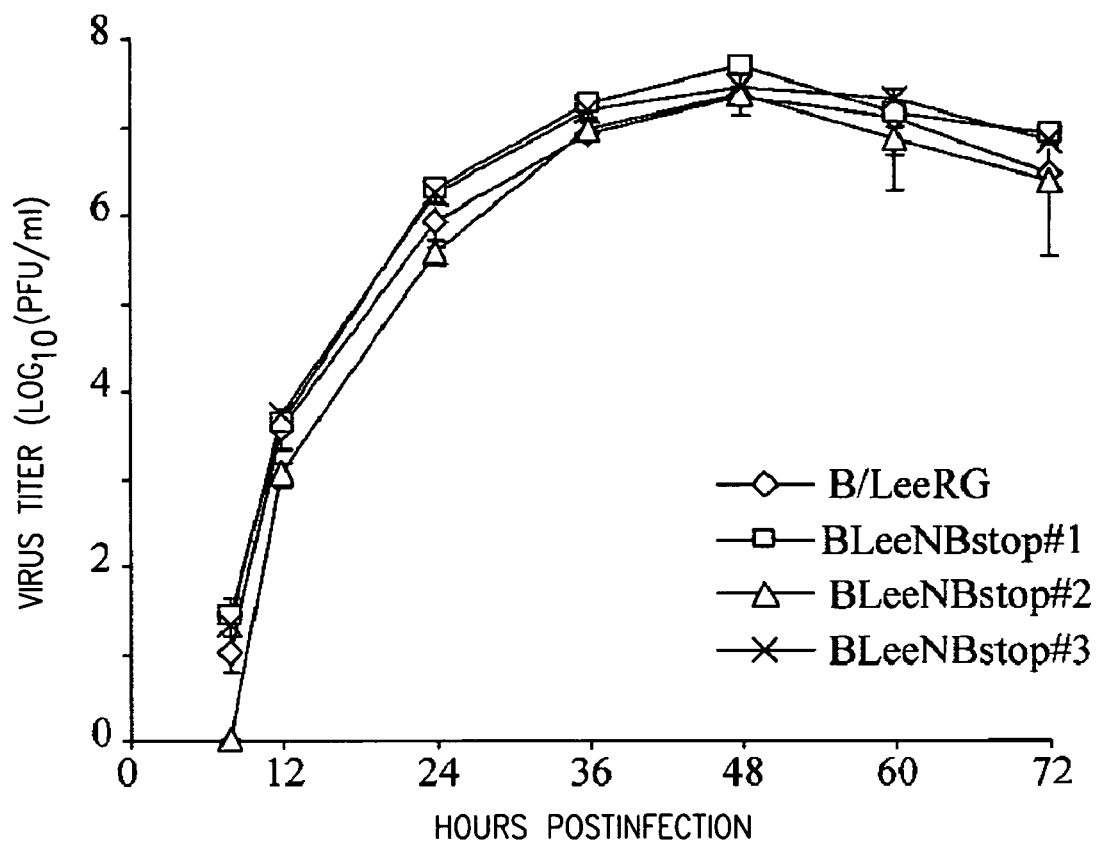

Growth properties of NB-knockout viruses in cell culture. MDCK cells were infected with B/LeeRG, BLeeNBstop#1, BLeeNBstop#2, or BLeeNBstop#3 viruses at an MOI of 0.001 PFU per cell and incubated at 37° C. The supernatants were collected at different times postinfection, and virus titers were determined by plaque assays in MDCK cells. BLeeNBstop#1, BLeeNBstop#2, and BLeeNBstop#3 viruses showed similar growth kinetics to those of B/LeeRG, with virus titers reaching $10^7$ PFU/ml at 36 hr postinfection (FIG. 6). These results indicate that, in cell culture, influenza B virus can undergo multiple cycles of replication and grow well without NB protein.

Replication of NB knockout viruses in mice. To determine the role of NB in influenza B virus replication in vivo, the $MLD_{50}$ of the wild-type and mutant viruses were compared (Table 5). The $MLD_{50}$ values for NB knockout viruses were at least one log higher than the value for B/LeeRG. In tests of virus replication in the lungs and nasal turbinates (NT) of mice infected with $10^4$ PFU of virus (Table 3), B/LeeRG grew well in both sites, while the growth of mutant viruses was restricted, as shown by virus titers that were generally more than one log lower than the titer for mutant viruses. Thus, although not required for growth in cell culture, the NB protein appears important for efficient influenza B virus replication in mice.

TABLE 3

Role of NB in virus replication in mice[a]

| Virus | Virus titer (mean log PFU ± SD/g) in: | | $MLD_{50}$ (PFU) |
|---|---|---|---|
| | Lungs | Nasal tubinates | |
| B/LeeRG | 7.9 ± 0.2 | 6.5 ± 0.2 | $2.1 \times 10^3$ |
| BLeNBstop#1 | 5.2 ± 0.6 | 4.9 ± 0.3 | $4.3 \times 10^4$ |
| BLeNBstop#2 | 5.7 ± 0.1 | 3.9 ± 0.2 | $>1.5 \times 10^5$ |
| BLeNBstop#3 | 6.6 ± 0.04 | 3.4 ± 0.4 | $1.5 \times 10^4$ |

[a]BALB/c mice, anesthetized with methoxyflurane, were infected intranasally with 50 µl of virus ($1 \times 10^4$ PFU). Three mice from each virus-infected group were sacrificed on day 3 postinfection for virus titration. The $MLD_{50}$ was determined as described in Gao et al. (1999).

Discussion

As shown herein above, the NB protein is not essential for influenza B virus replication in cell culture, but promotes efficient replication in vivo. In this regard, NB is similar to the M2 protein of A/WSN/33 influenza virus, although the requirement for NB during in vivo replication appears less stringent than that for the M2 protein. An A/WSN/33 mutant lacking the transmembrane and cytoplasmic domains of M2 was severely attenuated in mice (Watanabe et al., 2001), and a mutant of A/Udorn/72 (H3N2) lacking nucleotides encoding amino acid residues 29 to 31 of the M2 protein was attenuated even in cell culture (Takeda et al., 2001). Although the ion channel activity of M2 is experimentally well-established (Duff et al., 1992; Holsinger et al., 1994; Pinto et al., 1992; Sugrue et al., 1990; Sugrue et al., 1991), such activity has not been unequivocally demonstrated for the NB protein. Thus, the limited dependency of influenza B virus on NB function may suggest either that the virus does not depend as much on ion channel activity as influenza A virus does or that NB has functions other than ion channel activity. Since NB is highly conserved among influenza B strains, such function(s) must be important for viral replication in a natural setting.

Current human vaccines are inactivated vaccines that reduce the severity of, but are limited in their ability to prevent, viral infection. Clinical trials of cold-adapted live attenuated vaccines have generated promising results with respect to both efficacy and safety (Abbasi et al., 1995; Alexandrova et al., 1986; Anderson et al., 1992; Belshe et al., 1998; Cha et al., 2000; Hrabar et al., 1977; Obrosova-Serova et al., 1990; Steinhoff et al., 1990; Tomoda et al., 1995; Wright et al., 1982)). However, a molecular basis for the attenuation of the master vaccine strain of influenza B viruses remains unknown. Thus, it is important to produce an influenza B virus with known attenuating mutations. It would be ideal to produce a master vaccine strain which contains attenuating mutations exclusively in genes other than the HA and NA, so that only the latter genes need replacement with those of a field strain for vaccine production. However, with the invention of reverse genetics, it is no longer difficult to modify even the HA and NA genes for vaccine production. Thus, the mutations to knockout NB expression may be included, in addition to other attenuating mutations, into vaccine strains, considering that no growth defect was detected with NB knockout viruses in cell culture.

Although the replicative abilities of NB knockout viruses were similar to each other in MDCK cells, they differed in mice. This difference in replicative ability among the mutants in mice may originate from different levels of NA expression. To knockout NB expression, the upstream sequence of the NA protein was modified. This might have altered NA protein expression levels, resulting in varying extents of attenuation in vivo.

Thus far, five viral proteins have been reported to act as ion channels: M2 protein of influenza A virus, NB protein of influenza B virus, Vpu and Vpr of human immunodeficiency virus type 1 (HIV-1), and Kcv of chlorella virus (Ewart et al., 1996; Piller et al., 1996; Plugge et al., 2000; Schubert et al., 1996; Sugrue et al., 1990; Sugrue et al., 1991; Sunstrom et al., 1996). The Vpr and Kcv proteins have been demonstrated to play an important role in the viral life cycle. The Vpu gene of HIV-1 can be deleted without completely abrogating HIV-1 replication in vitro. In the present study, it was shown that NB protein is not necessary for viral growth in cell culture, but appears to be required for efficient influenza B virus replication in mice. Thus, NB mutations can be introduced, optionally with other attenuating mutations, into vaccine strains.

REFERENCES

Abbasi et al., *Virus. Res.*, 39:377 (1995).
Alberts et al., (eds) *Molecular Biology of the Cell*, Garland Publishing, Inc., New York, N.Y. (1994).
Albo et al., *J. Virol.*, 70:9013 (1996).
Alexandrova et al., *Vaccine*, 4:114 (1986).
Altschul et al., *J. Mol. Biol.* 215:403 (1990).
Altschul et al., *Nucleic Acids Res.* 25:3389 (1997).
Anderson et al., *J. Clin. Microbiol.*, 30:2230 (1992).
Appleyard, *J. Gen. Virol.*, 36:249 (1977).
*Avery's Drug Treatment: Principles and Practice of Clinical Pharmacology and Therapeutics*, 3rd edition, ADIS Press, Ltd., Williams and Wilkins, Baltimore, Md. (1987).
Aymard-Henry et al., *Virology: A Practical Approach*, Oxford IRL Press, Oxford, 119-150 (1985).
Bachmeyer, *Intervirology*, 5, 260-272 (1975).
Belshe et al., *N. Engl. J. Med.*, 338:1405 (1998).
Berkow et al., eds., *The Merck Manual*, 16th edition, Merck & Co., Rahway, N.J. (1992).
Betakova et al., *J. Gen. Virol.*, 77:2689 (1996).
Bilsel et al., *J. Virol.*, 67:6762 (1993).
Brassard et al., *Virology*, 220:350 (1996).
Bridgen et al., *Proc. Natl. Acad. Sci. U.S.A.*, 93:15400 (1996).
Castrucci et al., *J. Virol.*, 66:4647 (1992).
Castrucci et al., *J. Virol.*, 69:2725 (1995).
Cha et al., *J. Clin. Microbiol.*, 38:839 (2000).
Corpet et al., *Nucleic Acids Res.* 16:10881 (1988).
Cox et al., *Virology*, 167:554 (1988).
Daniels et al., *Cell*, 40:431 (1985).
Dedera et al., *J. Virol.*, 63:3205 (1989).
DuBridge et al., *Mol. Cell Biol.*, 7:379 (1987).
Duff et al., *FEBS Lett.*, 311:256 (1992).
Duff et al., *Virology*, 190:485 (1992).
Dunn et al., *Virology*, 211:133 (1995).
Edwards, *J. Infect. Dis.*, 169, 68-76 (1994).
Enami et al., *J. Virol.*, 65:2711 (1991).
Enami et al., *Proc. Natl. Acad. Sci. U.S.A.*, 87:3802 (1990).
Enami et al., *Virology*, 185:291 (1991).
Ewald et al., *J. Virol.*, 70:7108 (1996).
Ewart et al., *J. Virol.*, 70:7108 (1996).
Fischer et al., *Biochemistry*, 39:12708 (2000).
Fischer et al., *Eur. Biophys. J.*, 30:416 (2001).
Fodor et al., *J. Virol.*, 73:9679 (1999).
Gao et al., *J. Virol.*, 73:3184 (1999).
Goodman et al., eds., *Goodman and Gilman's The Pharmacological Basis of Therapeutics*, 8th edition, Pergamon Press, Inc., Elmsford, N.Y. (1990).
Goto et al., *Virology*, 238:265 (1997).
Grambas et al., *Virology*, 190:541 (1992).
Grand and Skehel, *Nature, New Biology*, 238, 145-147 (1972).
Hagen et al., *J. Virol.*, 68:1509 (1994).
Hay et al., *EMBO J.*, 4:3021 (1985).
Hay et al., In Hannoun, C., Kendal, A. P., Klenk, H. D., and Ruben, F. L. (eds) *Options for the control of influenza II*. Excerpta Medica, Amsterdam, pp. 281-288 (1993).
Helenius, *Cell*, 69:577 (1992).
Henikoff & Henikoff, *Proc. Natl. Acad. Sci. USA* 89:10915 (1989).
Higgins et al., *Gene* 73:237 (1988).
Higgins et al., *CABIOS* 5:151 (1989).
Huang et al., *CABIOS* 8:155 (1992).
Herlocher et al., *Proc. Natl. Acad. Sci. USA*, 90:6032 (1993).
Hoffmann et al., *J. Gen. Virol.*, 81:2843 (2000).
Hoffmann et al., *Proc. Natl. Acad. Sci. USA*, 99:11411 (2002).
Holsinger et al., *J. Virol.*, 68:1551 (1994).
Horimoto et al., *J. Virol.*, 68:3120 (1994).
Horimoto et al., *Virology*, 206:755 (1995).
Horimoto et al., *Virology*, 213:223 (1995).

Hrabar et al., *Dev. Biol. Stand.*, 39:53 (1977).
Jackson et al., *J. Virol.*, 76:11744 (2002).
Kato et al., *Virology*, 37:632 (1969).
Katz et al., *J. Virol.*, 64:1808 (1990).
Katzung, (ed.), *Basic and Clinical Pharmacology*, Fifth Edition, Appleton and Lange, Norwalk, Conn. (1992).
Kawaoka et al., *Virology*, 139:303 (1984).
Keitel et al., in *Textbook of Influenza*, eds. Nickolson, K. G., Webster, R. G., and Hay, A. (Blackwell, Oxford), pp. 373-390 (1998).
Kilbourne, *Bull. M2 World Health Org.*, 41, 653-645 (1969).
Klimkait et al., *J. Virol*, 64:621 (1990).
Kobasa et al., *J. Virol.*, 71:6706 (1997).
Lamb et al., In Fields, B. N., Knipe, D. M., and Howley, P. M. (eds) *Fields Virology*, 3rd ed. Lippincott-Raven Publishers, Philadelphia, Pa., pp. 1353-1395 (1996).
Laver & Webster, *Virology*, 69, 511-522 (1976).
Leahy et al., *J. Virol.*, 71:8347 (1997).
Leahy et al., *J. Virol.*, 71:8352 (1997).
Leahy et al., *J. Virol.*, 72:2305 (1998).
Lear et al., *Science*, 240:1177 (1988).
Li et al., *Virus Res.* 37:153 (1995).
Luytjes et al., *Cell*, 59:1107 (1989).
Maassab et al., *Rev. Med. Virol.*, 9:237 (1991).
Martin et al., *Cell*, 67:117 (1991).
Mena et al., *J. Virol.*, 70:5016 (1996).
Mizrahi, (ed.), *Viral Vaccines*, Wiley-Liss, New York, 39-67 (1990).
Murphy, *Infect. Dis. Clin. Pract.*, 2, 174-181 (1993).
Muster et al., *Proc. Natl. Acad. Sci. USA*, 88, 5177-5181 (1991).
Myers and Miller, *CABIOS* 4:11 (1988).
Needleman and Wunsch, *J. Mol. Biol.* 48:443 (1970).
Neirynck et al., *Nat. Med.*, 5: 1157 (1999).
Neumann et al., *J Virol.*, 71:9690 (1997).
Neumann et al., *Proc. Natl. Acad. Sci. USA*, 96:9345 (1999).
Neumann et al., *Virology*, 202:477 (1994).
Niwa et al., *Gene*, 108:193 (1991).
Obrosova-Serova et al., *Vaccine*, 8:57 (1990).
Ochman et al., *Genetics*, 120:621 (1988).
Ogra et al., *J. Infect. Dis.*, 134, 499-506 (1977).
Ohuchi et al., *J. Virol.*, 68:920 (1994).
Osol (ed.), *Remington's Pharmaceutical Sciences*, Mack Publishing Co., Easton, Pa. 1324-1341 (1980).
Pearson et al., *Meth. Mol. Biol.* 24:307 (1994).
Pearson and Lipman, *Proc. Natl. Acad. Sci.* 85:2444 (1988).
Perez et al., *Virology*, 249:52 (1998).
Piller et al., *Proc. Natl. Acad. Sci. USA*, 93:111 (1996).
Pinto et al., *Cell*, 69:517 (1992).
Pleschka et al., *J. Virol.*, 70:4188 (1996).
Plugge et al., *Science*, 287:1641 (2000).
Robertson et al., *Biologicals*, 20, 213-220 (1992).
Robertson et al., *Giornale di Igiene e Medicina Preventiva*, 29, 4-58 (1988).
Roizman et al., In Fields, B. N., Knipe, D. M., and Howley, P. M. (eds) *Fields Virology*, 3rd ed. Lippincott-Raven Publishers, Philadelphia, Pa., pp. 101-111 (1996).
Sansom et al., *Protein Eng.*, 6:65 (1993).
Schnell et al., *EMBO J.*, 13:4195 (1994).
Schubert et al., *FEBS Lett.*, 398:12 (1996).
Schubert et al., *J. Virol.*, 69:7699 (1995).
Sears et al., *J. Infect. Dis.*, 158:1209 (1988).
Shaw et al., *Proc. Natl. Acad. Sci. USA*, 80:4879 (1983).
Shaw et al., *Virology*, 139:178 (1984).
Smith et al., *Adv. Appl. Math.* 2:482 (1981).
Skehel et al., *J. Gen. Virol.*, 38:97 (1978).
Steinhoff et al., *J. Infect. Dis.*, 162:394 (1990).
Steinhoff et al., *J. Infect. Dis.*, 163:1023 (1991).
Strebel et al., *J. Virol.*, 63:3784 (1989).
Strebel et al., *Science* 241:1221 (1988).
Subbarao et al., *J. Virol.*, 67, 7223-7228 (1993).
Subbarao et al., *J. Virol.*, 67:7223-7228 (1993).
Sugrue et al., *EMBO J.*, 9:3469 (1990).
Sugrue et al., *Virology*, 180:617 (1991).
Sunstrom et al., *J. Membr. Biol.*, 150:127 (1996).
Takeda et al., *J. Virol.*, 76:1391 (2002).
Takeuchi et al., *J. Virol.*, 68:911 (1994).
Terwilliger et al., *Proc. Natl. Acad. Sci. USA*, 86:5163 (1989).
Tomoda et al., *Vaccine*, 13:185 (1995).
Tosteson et al., *Biosci. Rep.*, 8:173 (1988).
Tosteson et al., *Proc. Natl. Acad. Sci. USA*, 86:707 (1989).
Wang et al., *J. Virol.*, 67:5585 (1993).
Watanabe et al., *J. Virol.*, 75:5656 (2001).
Weber et al., *Arch. Virol*, 142:1029 (1997).
Weber et al., *J. Virol.*, 70:8361 (1996).
Wharton et al., *EMBO J.*, 14:240 (1995).
Williams et al., *Mol. Cell. Biol.*, 6:4317 (1986).
Williams et al., *Mol. Cell. Biol.*, 8:1186 (1988).
World Health Organization TSR No. 673 (1982)).
Wright et al., *J. Infect. Dis.*, 146:71 (1982).
Yasuda et al., *J. Virol.*, 68:8141 (1994).
Zebedee et al., *J. Virol.*, 62:2762 (1988).
Zhimov et al., *J. Gen. Virol.*, 65:1127 (1984).
Zhimov, *Virology*, 176:274 (1990).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated recombinant influenza B virus comprising a knockout mutation of the NB protein gene.

2. The isolated recombinant virus of claim 1 wherein the NB protein gene comprises at least two mutations, one of which is not in the transmembrane domain.

3. The isolated recombinant virus of claim 1 wherein at least one mutation is at the codon for the initiator methionine.

4. The isolated recombinant virus of claim 3 wherein at least one mutation encodes a substitution at the codon for the initiator methionine.

5. The isolated recombinant virus of claim 3 wherein at least one mutation in the mutant NB protein gene is a stop codon for the codon for the initiator methionine.

6. The isolated recombinant virus of claim 3 wherein at least one mutation in the mutant NB protein gene is a stop codon in the coding region for the membrane protein.

7. The isolated recombinant virus of claim 1 wherein the mutant NB protein gene comprises a deletion of one or more nucleotides.

8. The isolated recombinant virus of claim 7 wherein the deletion alters the reading frame for the NB protein.

9. The isolated recombinant virus of claim 1 wherein the mutant NB protein gene comprises an insertion of one or more nucleotides.

10. The isolated recombinant virus of claim 9 wherein the insertion alters the reading frame for the NB protein.

11. The isolated recombinant virus of claim 1 wherein the mutant NB protein gene comprises a deletion of one or more nucleotides and encodes an amino acid substitution.

12. The isolated recombinant virus of claim 1 wherein the mutant NB protein gene comprises an insertion of one or more nucleotides and encodes an amino acid substitution.

13. The isolated recombinant virus of claim 1 which further comprises a heterologous immunogenic protein of a pathogen or a therapeutic protein.

14. The isolated recombinant virus of claim 1 which further comprises a heterologous immunogenic protein gene of a pathogen or a therapeutic protein gene.

15. The isolated recombinant virus of claim 1 wherein the mutation does not alter the in vitro replication of the virus but is associated with attenuation of the virus in vivo.

16. A vaccine comprising the isolated recombinant virus of claim 1.

17. A method of preparing a recombinant influenza B virus comprising a knockout mutation of the NB protein gene comprising:

(i) contacting a host cell with a plurality of influenza vectors so as to yield recombinant influenza virus, wherein the plurality of vectors comprises: a) vectors to generate vRNA, comprising a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising promoter operably linked to an influenza virus NP cDNA linked to a transcription termination sequence, a vector comprising a promoter operably linked to an influenza virus cDNA for NB and NA linked to a transcription termination sequence, a vector comprising a promoter operably linked to an influenza virus M cDNA linked to a transcription termination sequence, a vector comprising a promoter operably linked to an influenza virus NS cDNA linked to a transcription termination sequence, wherein the sequence of the cDNA for NB and NA comprises a knockout mutation in the NB sequence, and b) vectors to express influenza virus proteins, comprising a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, and a vector comprising a promoter operably linked to a DNA segment encoding influenza virus NP, and optionally one or more vectors selected from a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M, and a vector comprising a promoter operably linked to a DNA segment encoding influenza virus NS2; and (ii) isolating the virus.

18. The method of claim 17 wherein the mutant NB protein gene encodes at least one amino acid substitution.

19. The method of claim 17 wherein the NB protein gene comprises at least two mutations, one of which is not in the transmembrane domain.

20. The method of claim 19 wherein at least one mutation in the mutant NB protein gene is a stop codon for the codon for the initiator methionine.

21. The method of claim 19 wherein at least one mutation in the mutant NB protein gene is a stop codon in the coding region for the NB protein.

22. The method of claim 17 wherein at least one mutation is at the codon for the initiator methionine.

23. The method of claim 17 wherein the mutant NB protein gene comprises a deletion of one or more nucleotides.

24. The method of claim 23 wherein the deletion alters the reading frame for the NB protein.

25. The method of claim 17 wherein the mutant NB protein gene comprises an insertion of one or more nucleotides.

26. The method of claim 25 wherein the insertion alters the reading frame for the NB protein.

27. The method of claim 17 wherein the mutant NB protein gene encodes a substitution at the initiator methionine.

28. The method of claim 17 wherein the mutant NB protein gene comprises a deletion of one or more nucleotides and encodes at least one amino acid substitution.

29. The method of claim 17 wherein the mutant NB protein gene comprises an insertion of one or more nucleotides and encodes an amino acid substitution.

30. Isolated virus prepared by the method of claim 17.

31. An isolated host cell contacted with the virus of claim 1 or 30.

32. A method to immunize a vertebrate, comprising: contacting the vertebrate with an effective amount of the recombinant virus of claim 1.

33. The method of claim 32 wherein the vertebrate is an avian.

34. The method of claim 32 wherein the vertebrate is a mammal.

35. The method of claim 32 wherein the vertebrate is a human.

36. A composition comprising a plurality of influenza B vectors, comprising: a) vectors to generate vRNA, comprising a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising promoter operably linked to an influenza virus NP cDNA linked to a transcription termination sequence, a vector comprising a promoter operably linked to an influenza virus cDNA for NB and NA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein the sequence of the cDNA for NB and NA comprises a knockout mutation in the sequence for NB the presence of which in the mutant gene optionally yields a functional NA protein; and b) vectors to express influenza virus proteins, comprising a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, and a vector comprising a promoter operably linked to a DNA segment encoding influenza virus NP.

37. The composition of claim 36 further comprising a vector to generate vRNA comprising a promoter operably linked to a DNA fragment of interest in antisense orientation.

38. The composition of claim 37 wherein the vector comprises a DNA fragment which encodes an immunogenic polypeptide or peptide of a pathogen or a therapeutic protein.

39. The composition of claim 36 wherein the NB protein gene comprises at least two mutations, one of which is not in the transmembrane domain.

40. The composition of claim 39 wherein at least one mutation is in the codon for the initiator methionine.

* * * * *

UNITED STATES PATENT AND TRADEMARK OFFICE
CERTIFICATE OF CORRECTION

Page 1 of 1

PATENT NO. : 7,588,769 B2
APPLICATION NO. : 10/827995
DATED : September 15, 2009
INVENTOR(S) : Yoshihiro Kawaoka It is certified that error appears in the above-identified patent and that said Letters Patent is hereby corrected as shown below:

In the Specification

Column 1, Lines 13-16:
Delete the phrase:
"This invention was made with a grant from the Government of the United States of America (grant AI-47446 from the National Institutes of Health). The Government may have certain rights in the invention."

And replace with:
--This invention was made with government support under AI047446 awarded by the National Institutes of Health. The government has certain rights in the invention.--.

Signed and Sealed this
Eighth Day of December, 2020

Andrei Iancu
*Director of the United States Patent and Trademark Office*

SEQUENCE LISTING

<160> NUMBER OF SEQ ID NOS: 29

<210> SEQ ID NO 1
<211> LENGTH: 2396
<212> TYPE: DNA
<213> ORGANISM: Influenza virus B/Lee/40

```
<400> SEQUENCE: 1
agcagaagcg gagcgttttc aagatgacgt tggctaaaat tgaactacta aagcagctgt      60
taagggacaa tgaagccaaa acggtgttga gacagacaac ggtagaccaa tacaacataa     120
taagaaaatt caatacatca agaattgaaa agaaccctte attaagaatg aagtgggcca     180
tgtgttccaa ttttccctta gctctgacca agggtgatat ggcaaatcga atccccttgg     240
aatacaaggg aatacaactt aaaacaaatg ctgaagacat aggaactaaa ggacaaatgt     300
gttcaatagc agcagttacc tggtggaata catatgggcc catagggat actgaagggt      360
ttgaaaaggt ctacgaaagc ttttttctca gaaagatgag acttgacaat gccacttggg     420
gccgaatgac ctttggccct gttgagagag taagaaaaag agtactacta aacccgctca     480
ccaaggaaat gccccagat gaagcgagca atgtaataat ggaaatatta ttccctaaag      540
aagcaggaat accaagagaa tctacttgga tacatagaga actgataaaa gaaaaagag      600
aaaaattgaa gggaacgatg ataactccca ttgtactggc atacatgctt gagagagaac     660
tagttgcccg aagaaggttc ctgccagtag caggagcaac atcagcagag ttcatagaaa     720
tgctacattg cttacaaggt gaaaattgga gacaaatata tcatccagga gggaataaac     780
taactgaatc tagatctcaa tcaatgattg tagcttgcag gaagataatc agaagatcaa     840
tagttgcatc aaacccacta gagctagctg tagagattgc aaataagact gtgatagaca     900
ctgaaccttt aaagtcatgt ctggcagccc tagatggagg tgatgtagcc tgtgacataa     960
taagagctgc attaggatta aaaattagac aaagacaaag atttggagag cttgaactaa    1020
agagaatatc agggagagga ttcaaaaatg atgaagagat attaatcgga aacggaacaa    1080
tacaaaagat tggaatatgg gacggagaag aggaattcca tgtaagatgt ggtgaatgca    1140
gggggatatt gaaaaaagc aaaatgagaa tggaaaaact actgataaat tcagccaaaa     1200
aggaggacat gaaagattta ataatcttat gcatggtatt ttctcaagac accaggatgt    1260
tccaaggagt gagaggagag ataaattttc ttaatcgagc aggccaactt ttatccccca    1320
tgtaccaact ccaacgatac ttttttgaata ggagcaatga ccttttttgat caatgggat    1380
atgaggaatc acctaaagca agtgagctac atgggataaa tgaattaatg aatgcatctg    1440
actatacatt gaagggggtt gtagtaacaa aaatgtgat tgatgatttt agttctactg     1500
aaacagaaaa agtatctata acaaaaaatc ttagtttaat aaaaaggact ggggaagtta    1560
taatgggagc caatgacgta agtgaattag aatcacaagc acagctaatg ataacgtatg    1620
atacacccaa gatgtgggaa atgggaacaa ccaaagaact ggtacaaaac acttaccaat    1680
gggtgcttaa aaatttagta acattgaagg ctcagttttct tttgggaaaa gaagacatgt    1740
tccaatggga tgcatttgaa gcatttgaaa gcataatccc tcagaagatg gctggtcagt    1800
acagtggatt tgcaagagca gtgctcaaac aaatgagaga ccaagaggtt atgaaaactg    1860
accaattcat aaaaattgttg cctttctgtt tttcgccacc aaaattaagg agcaatggag    1920
agccttatca ttttttgagg cttatgctga aggaggagg ggaaaatttc atcgaagtaa     1980
ggaaagggtc ccccttgttc tcctacaatc acaaacgga atcctaact atatgcggca      2040
gaatgatgtc attaaaagga aaaattgagg atgaagaaag aaatagatca atggggaatg    2100
cagtactggc aggctttctt gttagtggca atatgaccc agatcttgga gatttcaaa     2160
ccattgagga acttgaaaga ctaaaaccgg agaaaaagc caacatctta ctttaccaag    2220
gaaagccgt taaagtagtt aaaaggaaaa gatatagtgc tttatccaat gatatttcac     2280
aagggattaa gagacaaaga atgacagttg agtccatggg gtgggccttg agctaatata    2340
```
aatttatcca tcaattcaat aaatacaatt gagtgaaaaa tgctcgtgtt tctact      2396

<210> SEQ ID NO 2
<211> LENGTH: 2368
<212> TYPE: DNA
<213> ORGANISM: Influenza virus B/Lee/40

<400> SEQUENCE: 2
agcagaagcg gagctttaag atgaatataa atccatattt tcttttcata gatgtaccta      60
tacaggcagc aatttcaaca acattcccat acaccggtgt tcccccttat tctcatggaa     120
cgggaacagg ctacacaata gacaccgtga ttagaacaca cgagtactca aacaagggaa     180
aacaatacat ttctgatgtt acaggatgtg taatggtaga tccaacaaat gggccattac     240
ccgaagacaa tgaaccgagt gcctatgcac aattggattg tgttctggag ctttggata      300
gaatggatga gaacatcca ggtctgtttc aagcagcctc acagaatgcc atggaggcac      360
taatggtcac aacagtggac aaattgactc aggggagaca gacctttgat tggacggtgt     420
gtagaaacca acctgctgca acggcactga acacaacaat aaactctttt aggttgaatg     480
atttaaatgg agccgacaag ggtggattag tgccctttg ccaagatatc attgattcat     540
tagacaaacc tgaaatgatt ttcttctcag taaagaatat aaagaaaaaa ttgcctgcta     600
aaaacagaaa gggttttcctt ataaaaagaa tacctatgaa ggtaaaagac agaataacaa     660
gagtggaata catcaaaaga gcattatcat taaacacaat gactaaagat gctgaaagag     720
gcaaactaaa aagaagagca attgccaccg ctgggataca aatcagagga tttgtattag     780
tagttgaaaa cttggctaaa aatatctgtg aaaatctaga gcaaagtggt ttacccgtag     840
gtgggaacga aaagaaggcc aaactatcaa atgcagtggc taaaatgctc agtaattgtc     900
caccaggagg gatcagtatg actgtgacag agacaatac taaatggaat gaatgcttaa     960
atccaagaat ctttttggct atgactgaaa gaataaccag agacagccca atttggttcc    1020
gggattttg tagtatagca ccggtcttgt tctccaataa aatagctaga ttgggaaaag    1080
ggttcatgat aacaagtaaa acaaaaagac taaaagctca ataccttgt cccgatctgt    1140
ttaatatacc attagaaaga tataatgaag aaacaagggc aaaactgaaa agctaaaac    1200
ctttcttcaa tgaagaagga acggcatctc tttcgccagg aatgatgatg gaatgtttta    1260
atatgctatc tacagtatta ggagtagccg cactagggat aaaaaacatt ggaaacaaag    1320
aatacttatg gatggactg cagtcttccg atgattttgc tctgtttgtt aatgcaaaag    1380
atgaagagac atgtatggaa ggaataaacg atttttaccg aacatgtaag ctattgggaa    1440
taaacatgag caaaaagaaa agttactgta atgaaactgg gatgtttgaa tttaccagca    1500
tgttttacag agatggattt gtatctaatt ttgcaatgga actccttca tttggagtcg    1560
ctggagtgaa tgaatcagca gacatggcaa taggaatgac aataataaag aacaatatga    1620
tcaacaatgg gatgggccca gcaacggcac aaacagccat acaattattc atagctgatt    1680
atagatacac ctacaaatgc cacagggag attccaaagt ggaagggaag agaatgaaaa    1740
ttataaagga gctatgggaa aacactaaag gaagagatgg tctattagta gcagatggtg    1800
ggcctaatct ttcaatttg agaaacctgc atattccaga aatagtatta aaatacaaca    1860
taatggaccc tgagtacaaa ggacggttac tgcatcctca aaatcccttt gtaggacatt    1920
tgtctattga gggtatcaaa gaagcagata acacctgc acatggccca ataagaaaa    1980
tggactacga tgcggtatct ggaactcata gttggagaac caaaggaac agatctatac    2040

-continued

```
taaacactga tcagaggaac atgattcttg aggaacaatg ctacgctaag tgttgcaacc      2100
tttttgaggc ttgctttaac agtgcgtcat acaggaaacc agtaggccag cacagcatgc      2160
ttgaagctat ggcccacaga ttaagaatgg atgcacgact ggactatgag tcaggaagga      2220
tgtcaaaaga ggatttcgaa aaagcaatgg ctcaccttgg tgagattggg tacatgtaag      2280
ctccggaaat gtctatgggg ttattggtca tcgttgaata catgcggtgc acaaatgatt      2340
aaaatgaaaa aaggctcgtg tttctact                                        2368
```

<210> SEQ ID NO 3
<211> LENGTH: 2307
<212> TYPE: DNA
<213> ORGANISM: Influenza virus B/Lee/40

<400> SEQUENCE: 3

```
agcagaagcg gtgcgtttga tttgccacaa tggatacttt tattacaaag aatttccaga       60
ctacaataat acaaaaggcc aaaaacacaa tggcagaatt tagtgaagat cctgaattac      120
agccagcagt actattcaac atctgcgtcc atctggaggt ctgctatgta ataagtgata      180
tgaactttct tgatgaggaa ggaaagacat atacagcatt agaaggacaa ggaaaagagc      240
aaaatttgag accacagtat gaagtgattg agggaatgcc aagaaacata gcatggatgg      300
ttcaaagatc cttagcccaa gagcatggaa tagagactcc aaggtatctg ctgatttat       360 ttgattataa aaccaagagg tttatcgaag tcggagtaac aaagggattg gctgatgatt      420
acttttggaa aaagaaagaa agtgggggga atagcatgga actgatgata ttcagctata      480
atcaagacta ctcgttaagt gatgaatctt cattggatga ggaaggaaaa gggagagtgc      540
taagcagact cacagaactt caggctgagt taagtttgaa aaacctatgg caagttctaa      600
taggggaaga agaaattgaa aaaggaattg acttcaaact tggacaaaca atatctaaac      660
tgagggatat atctgttcca gctggttttc ccaattttga agggatgaga agttacatag      720
acaacataga ccctaaagga gcaatagaga gaaatctagc aaggatgtct cccttagtat      780
cagttacacc caaaaagttg aaatggggagg acctgagacc catagggcct cacatttaca      840
accatgagct accagaagtt ccatataatg cctttctcct catgtctgat gagttggggc      900
tggccaatat gactgaagga aagtccaaga accgaagac cttagctaag gaatgtctag      960
aaaggtattc aacactacgt gatcaaactg acccaatatt gataatgaaa gcgaaaaag    1020 ctaacgaaaa cttcttatgg aggttatgga gggactgtgt aaatacaata agcaatgagg      1080
aaacaggcaa cgaattacag aaaccaatt atgccaagtg ggccacagga gatggactaa     1140
cataccaaaa aataatgaaa gaagtagcaa tagatgacga aacgatgtac caagaagaac      1200
ccaaaatacc caataaatgt agagtggctg cttgggttca ggcagagatg aatctactga      1260
gtactctgac aagtaaaagg gcccctggatc tgccagaaat agggcagat gtagcacccg      1320 tggagcatgt agggagtgaa agaaggaaat actttgttaa tgaaatcaac tactgtaaag      1380
cctctacagt tatgatgaag tatgtacttt ttcacacttc attattaaat gaaagcaatg      1440
ctagtatggg aaaatataaa gtaataccaa tcaccaacag agtggtaaat ggaaaagggg      1500
aaagctttga catgctttat ggtctggcgg ttaaggggca atctcatttg cggggggaca      1560
cggatgttgt aacagttgtg actttcgagt ttagtagtac agatcctaga gtggactcag      1620
gaaagtggcc aaaatatact gtctttaaaa ttggctccct atttgtgagt ggaagagaaa      1680
aacctgtgta cctatattgc cgagtgaatg gtacaaacaa aatccaaatg aaatgggaa      1740 tggaagctag aagatgtctg cttcaatcaa tgcaacaaat ggaggcaatt gttgatcaag      1800
```

```
aatcatcgat acaagggtat gatatgacca aagcttgttt caagggagac agagtgaata   1860
atcccaaaac tttcagtatt gggactcagg aaggcaaact agtaaaaggg tcctttggga   1920
aagcactaag agtaatattc accaaatgtt tgatgcatta tgtatttgga aatgctcaat   1980 tggagggggtt tagtgccgaa tctaggagac ttctactgtt aattcaggca ttaaaagaca   2040
ggaagggccc ttgggtattt gacttagagg aatgtactc tggagtagag aatgtatta    2100
```

```
ctagacagga tagctgctgg caccttaat gcaggagatt tttctcttcc cactttgat      1620 tcattaaaca ttactgctgc atctttaaat gatgatggct tggataatca tactatactg      1680
ctctactact caactgctgc ttctagcttg gctgtaacat tgatgatagc tatcttcatt      1740
gtctacatgg tctccagaga caatgtttct tgttccatct gtctgtgagg gagattaagc      1800
cctgtgtttt cctttactgt agtgctcatt tgcttgtcac cattacaaag aaacgttatt      1860
gaaaaatgct cttgttacta ct                                               1882
```

<210> SEQ ID NO 5
<211> LENGTH: 1557
<212> TYPE: DNA
<213> ORGANISM: Influenza virus B/Lee/40

<400> SEQUENCE: 5

```
agcagaagca gagcatattc ttagaactga agtgaacagg ccaaaaatga acaatgctac       60
cttcaactgt acaaacatta accctattac tcacatcagg gggagtatta ttatcactat      120
atgtgtcagc ctcattgtca tacttattgt attcggatgt attgctaaaa ttttcatcaa      180
caaaaacaac tgcaccaaca atgtcattag agtgcacaaa cgcatcaaat gcccagactg      240
tgaaccattc tgcaacaaaa gagatgacat ttccaccccc agagccggag tggacatacc      300
ctcgtttatc ttgccagggc tcaacctttc agaaggcact cctaattagc cctcataggt      360
tcggagagat caaggaaac tcagctccct tgataataag gaaccttttt gttgcttgtg       420
gaccaaaaga atgcagacac tttgctctga cccattatgc agctcagccg ggggatact       480 acaatggaac aagaaggac agaaacaagc tgaggcatct agtatcagtc aaattgggaa       540
aaatcccaac tgtggaaaac tccattttcc acatggcagc ttggagcgga tccgcatgcc       600
atgatggtag agaatggaca tatatcggag ttgatggtcc tgacaatgat gcattggtca       660
aaataaaata tggagaagca tatactgaca catatcattc ctatgcacac aacatcctaa       720
gaacacaaga aagtgcctgc aattgcatcg ggggagattg ttatcttatg ataacagacg       780
gctcagcttc aggaattagt aaatgcagat tccttaaaat tagagagggt cgaataataa       840
aagaaatact tccaacagga gagtggagc acactgaaga gtgcacatgc gggttcgcca       900
gcaataaaac catagaatgt gcctgtagag acaacagtta cacagcaaaa agaccctttg       960
tcaaattaaa tgtggaaact gatacagctg aaataagatt gatgtgcaca aagacttatc      1020
tggacactcc cagaccggat gatggaagca tagcagggcc ttgcgaatct aatggagaca      1080
agtggcttgg aggcatcaaa ggaggatttg tccatcaaag aatggaatct aagattggaa      1140
gatggtactc ccgaacgatg tctaaaacta cagaatggg gatggaactg tatgtaaagt       1200
atgatggtga cccatggact gacagtgatg ctcttactct tagtggagta atggtttcca      1260
tagaagaacc tggttggtat tcttttggct tcgaaataaa ggacaagaaa tgtgatgtcc      1320
cttgtattgg gatagagatg gtacgcgatg gtggaaaaga tacttggcat tcagctgcaa      1380
cagccattta ctgtttgatg ggctcaggac aattgctatg gacactgtc acaggcgttg       1440 atatggcttt ataatagagg aatggttgga tctgttctaa accctttgtt cctatttat       1500 ttgaacagtt gttcttacta gatttaattg tttctgaaaa atgctcttgt tactact          1557
```

<210> SEQ ID NO 6
<211> LENGTH: 1841
<212> TYPE: DNA
<213> ORGANISM: Influenza virus B/Lee/40

<400> SEQUENCE: 6

-continued

```
agcagaagca cagcatttc ttgtgagctt cgagcactaa taaaactgaa aatcaaaatg      60
tccaacatgg atattgacag tataaatacc ggaacaatcg ataaaacacc agaagaactg    120
actcccggaa ccagtggggc aaccagacca atcatcaagc cagcaaccct tgctccgcca    180
agcaacaaac gaacccgaaa tccatcccca gaaaggacaa ccacaagcag tgaaaccaat    240
atcggaagga aaatccaaaa gaaacaaacc ccaacagaga taagaagag cgtctacaac     300
atggtggtaa aactgggtga attctacaac cagatgatgg tcaaagctgg acttaatgat    360
gacatggaaa ggaatctaat ccaaaatgca caagctgtgg agagaatcct attggctgca    420
actgatgaca agaaaactga ataccaaaag aaaaggaatg ccagagatgt caaagaaggg    480
aaagaagaaa tagaccacag caagacagga ggcacctttt ataagatggt aagagatgat    540
aaaaccatct acttcagccc tataaaaatt acctttttaa aagaagaggt gaaaacaatg    600
tataagacca ccatggggag tgatggtttc agtggactaa atcacattat gattggacat    660
tcacagatga acgatgtctg tttccaaaga tcaaggcac tgaaagggt tggacttgac     720
ccttcattaa tcagtacttt tgccggaagc acactaccca agatcagg tacaactggt     780
gttgcaatca aaggaggtgg aactttagtg gcagaagcca tccgatttat aggaagagca    840
atggcagaca gagggctact gagagacatc aaggccaaga cggcctatga aaagattctt    900
ctgaatctga aaacaagtg ctctgcgcct caacaaaagg ctctagttga tcaagtgatc    960
ggaagtagga acccagggat tgcagacata aagacctaa ctctgcttgc cagaagcatg    1020
gtagttgtca gaccctctgt agcgagcaaa gtggtgcttc ccataagcat ttatgctaaa    1080
atacctcaac taggattcaa tatcgaagaa tactctatgg ttgggtatga agccatggct    1140
ctttataata tggcaacacc tgtttccata ttaagaatgg gagatgacgc aaaagataaa    1200
tctcaactat tcttcatgtc gtgcttcgga gctgcctatg aagatctaag agtgttatct    1260
gcactaacgg gcaccgaatt taagcctaga tcagcactaa aatgcaaggg tttccatgtc    1320
ccggctaagg agcaagtaga aggaatgggg gcagctctga tgtccatcaa gcttcagttc    1380
tgggcccaa tgaccagatc tggagggaat gaagtaagtg gagaaggagg gtctggtcaa    1440
ataagttgca gccctgtgtt tgcagtagaa agacctattg ctctaagcaa gcaagctgta    1500
agaagaatgc tgtcaatgaa cgttgaagga cgtgatgcag atgtcaaagg aaatctactc    1560
aaaatgatga atgattcaat ggcaaagaaa accagtggaa atgctttcat tgggaagaaa    1620
atgtttcaaa tatcagacaa aaacaaagtc aatcccattg agattccaat taagcagacc    1680
atccccaatt tcttctttgg agggacaca gcagaggatt atgatgacct cgattattaa    1740
agcaataaaa tagacactat ggctgtgact gtttcagtac gtttgggatg tgggtgttta    1800
ctcttattga aataaatgta aaaaatgctg ttgtttctac t                        1841
```

<210> SEQ ID NO 7
<211> LENGTH: 1191
<212> TYPE: DNA
<213> ORGANISM: Influenza virus B/Lee/40

<400> SEQUENCE: 7

```
agcagaagca cgcactttct taaaatgtcg ctgtttggag acacaattgc ctacctgctt      60
tcactaatag aagatggaga aggcaaagca gaactagctg aaaaattaca ctgttggttc    120
ggtgggaaag aatttgacct agattctgct ttggaatgga taaaaaacaa aaggtgccta    180
actgatatac aaaaagcact aattggtgcc tctatatgct ttttaaaacc caaagaccaa    240
```

-continued

```
gaaagaaaaa ggagattcat cacagagccc ctgtcaggaa tgggaacaac agcaacaaag      300
aagaaaggcc taattctagc tgagagaaaa atgagaagat gtgtaagctt tcatgaagca      360
tttgaaatag cagaaggcca cgaaagctca gcattactat attgtcttat ggtcatgtac      420
ctaaaccctg aaaactattc aatgcaagta aaactaggaa cgctctgtgc tttatgcgag      480
aaacaagcat cgcactcgca tagagcccat agcagagcag caaggtcttc ggtacctgga      540
gtaagacgag aaatgcagat ggtttcagct atgaacacag aaagacaat gaatggaatg      600 ggaaagggag aagacgtcca aaaactagca gaagagctgc aaaacaacat tggagtgttg      660
agatctctag gagcaagtca aaagaatgga gaaggaattg ccaagatgt aatggaagtg       720 ctaaaacaga gctctatggg aaattcagct cttgtgagga atacttata atgctcgaac       780 cacttcagat tctttcaatt tgttctttca ttttatcagc tctccatttc atggcttgga      840
caatagggca tttgaatcaa ataagaagag gggtaaacct gaaaatacaa ataaggaatc      900
caaataagga ggcaataaac agagaggtgt caattctgag acacaattac caaaaggaaa      960
tccaagccaa agaaacaatg aagaaaatac tctctgacaa catggaagta ttgggtgacc     1020
acatagtagt tgaagggctt tcaactgatg agataataaa aatgggtgaa acagttttgg     1080
aggtggaaga attgcaatga gcccaatttt cactgtattt cttactatgc atttaagcaa     1140
attgtaatca atgtcagtga ataaaactgg aaaaagtgcg ttgtttctac t              1191
```

<210> SEQ ID NO 8
<211> LENGTH: 1096
<212> TYPE: DNA
<213> ORGANISM: Influenza virus B/Lee/40

<400> SEQUENCE: 8

```
agcagaagca gaggatttat ttagtcactg gcaaacggaa agatggcgga caacatgacc       60
acaacacaaa ttgaggtggg tccgggagca accaatgcca ctataaactt tgaagcagga      120
attctggagt gctatgaaag gttttcatgg caaagagccc ttgactatcc tggtcaagac      180
cgcctacaca gactaaaacg aaaattagaa tcaagaataa agactcacaa caagagtgag      240
cctgagaata aaaggatgtc tcttgaagag agaaaagcaa ttggggtaaa aatgatgaaa      300
gtgcttctgt ttatggatcc ctctgctgga attgaagggt tgagccata ctgtgtgaaa       360 aatccctcaa ctagcaaatg tccaaattac gattggaccg attaccctcc aaccccagga      420
aagtaccttg atgacataga agaagagccg gaaaatgtcg atcacccaat tgaggtagta      480
ttaagggaca tgaacaataa agatgcacga caaaagataa aggatgaagt aaacactcag      540
aaagagggga aattccattt gacaataaaa agggatatac gtaatgtgtt gtccttgaga      600
gtgttggtga acggaacctt cctcaagcac cctaatggag acaagtcctt atcaactctt      660
catagattga atgcatatga ccagaatgga gggcttgttg ctaaacttgt tgctactgat      720
gatcttacag tggaggatga aaaagatggc catcggatcc tcaactcact cttcgagcgt      780
tttgatgaag acattcaaa gccaattcga gcagctgaaa ctgcggtggg agtcttatcc      840
caatttggtc aagagcaccg attatcacca gaagagggga caattagac tggccacgga      900 agaactttat ctcttgagta aaagaattga tgatagtata ttgttccaca aacagtaat       960 agctaacagc tccataatag ctgacatgat tgtatcatta tcattactgg aaacattgta     1020
tgaaatgaag gatgtggttg aagtgtacag caggcagtgc ttatgaatgt aaaataaaaa     1080
tcctcttgtt actact                                                     1096
```

```
<210> SEQ ID NO 9
<211> LENGTH: 14
<212> TYPE: PRT
<213> ORGANISM: Artificial Sequence
<220> FEATURE:
<223> OTHER INFORMATION: A synthetic peptide.

<400> SEQUENCE: 9

Asn Lys Arg Asp Asp Ile Ser Thr Pro Arg Ala Gly Val Asp
 1               5                  10

<210> SEQ ID NO 10
<211> LENGTH: 33
<212> TYPE: DNA
<213> ORGANISM: Artificial Sequence
<220> FEATURE:
<223> OTHER INFORMATION: A synthetic oligonucleotide.

<400> SEQUENCE: 10
gggttattgg agacggtacc gtctcctccc ccc                          33

<210> SEQ ID NO 11
<211> LENGTH: 33
<212> TYPE: DNA
<213> ORGANISM: Artificial Sequence
<220> FEATURE:
<223> OTHER INFORMATION: A synthetic oligonucleotide.

<400> SEQUENCE: 11 gggggggagga gacggtaccg tctccaataa ccc                         33

<210> SEQ ID NO 12
<211> LENGTH: 17
<212> TYPE: DNA
<213> ORGANISM: Artificial Sequence
<220> FEATURE:
<223> OTHER INFORMATION: A synthetic oligonucleotide.
<220> FEATURE:
<221> NAME/KEY: misc_feature
<222> LOCATION: 11
<223> OTHER INFORMATION: N = A, T G or C

<400> SEQUENCE: 12
ttttgctccc ngagacg                                            17

<210> SEQ ID NO 13
<211> LENGTH: 17
<212> TYPE: DNA
<213> ORGANISM: Artificial Sequence
<220> FEATURE:
<223> OTHER INFORMATION: A synthetic oligonucleotide.
<220> FEATURE:
<221> NAME/KEY: misc_feature
<222> LOCATION: 7
<223> OTHER INFORMATION: n = A, T, G or C

<400> SEQUENCE: 13
cgtctcnggg agcaaaa                                            17

<210> SEQ ID NO 14
<211> LENGTH: 11
<212> TYPE: DNA
<213> ORGANISM: Artificial Sequence
<220> FEATURE:
<223> OTHER INFORMATION: A synthetic oligonucleotide.

<400> SEQUENCE: 14
tattagtaga a                                                  11
```

<210> SEQ ID NO 15
<211> LENGTH: 10
<212> TYPE: DNA
<213> ORGANISM: Artificial Sequence
<220> FEATURE:
<223> OTHER INFORMATION: A synthetic oligonucleotide.

<400> SEQUENCE: 15
gggagcaaaa                                                              10

<210> SEQ ID NO 16
<211> LENGTH: 15
<212> TYPE: DNA
<213> ORGANISM: Artificial Sequence
<220> FEATURE:
<223> OTHER INFORMATION: A synthetic oligonucleotide.

<400> SEQUENCE: 16
gggttattag tagaa                                                        15

<210> SEQ ID NO 17
<211> LENGTH: 15
<212> TYPE: DNA
<213> ORGANISM: Artificial Sequence
<220> FEATURE:
<223> OTHER INFORMATION: A synthetic oligonucleotide.

<400> SEQUENCE: 17
ttctactaat aaccc                                                        15

<210> SEQ ID NO 18
<211> LENGTH: 13
<212> TYPE: DNA
<213> ORGANISM: Artificial Sequence
<220> FEATURE:
<223> OTHER INFORMATION: A synthetic oligonucleotide.

<400> SEQUENCE: 18
ttttgctccc ccc                                                          13

<210> SEQ ID NO 19
<211> LENGTH: 13
<212> TYPE: DNA
<213> ORGANISM: Artificial Sequence
<220> FEATURE:
<223> OTHER INFORMATION: A synthetic oligonucleotide.

<400> SEQUENCE: 19 gggggggagca aaa                                                         13

<210> SEQ ID NO 20
<211> LENGTH: 22
<212> TYPE: DNA
<213> ORGANISM: Influenza virus B/Lee/40

<400> SEQUENCE: 20
gccaaaaatg aacaatgcta cc                                                22

<210> SEQ ID NO 21
<211> LENGTH: 11
<212> TYPE: DNA
<213> ORGANISM: Influenza virus B/Lee/40

<400> SEQUENCE: 21

```
ctaaaattttt a                                                          11

<210> SEQ ID NO 22
<211> LENGTH: 22
<212> TYPE: DNA
<213> ORGANISM: Artificial Sequence
<220> FEATURE:
<223> OTHER INFORMATION: A synthetic oligonucleotide.

<400> SEQUENCE: 22
gccaaaagcg aacaatgcta cc                                               22

<210> SEQ ID NO 23
<211> LENGTH: 11
<212> TYPE: DNA
<213> ORGANISM: Artificial Sequence
<220> FEATURE:
<223> OTHER INFORMATION: A synthetic oligonucleotide.

<400> SEQUENCE: 23
cttaaatttt a                                                           11

<210> SEQ ID NO 24
<211> LENGTH: 21
<212> TYPE: DNA
<213> ORGANISM: Artificial Sequence
<220> FEATURE:
<223> OTHER INFORMATION: A synthetic oligonucleotide.

<400> SEQUENCE: 24
gccaaaagcg acaatgctac c                                                21

<210> SEQ ID NO 25
<211> LENGTH: 11
<212> TYPE: DNA
<213> ORGANISM: Artificial Sequence
<220> FEATURE:
<223> OTHER INFORMATION: A synthetic oligonucleotide.

<400> SEQUENCE: 25
cttaaatttt a                                                           11

<210> SEQ ID NO 26
<211> LENGTH: 23
<212> TYPE: DNA
<213> ORGANISM: Artificial Sequence
<220> FEATURE:
<223> OTHER INFORMATION: A synthetic oligonucleotide.

<400> SEQUENCE: 26
gccaaaagcg aaacaatgct acc                                              23

<210> SEQ ID NO 27
<211> LENGTH: 11
<212> TYPE: DNA
<213> ORGANISM: Artificial Sequence
<220> FEATURE:
<223> OTHER INFORMATION: A synthetic oligonucleotide.

<400> SEQUENCE: 27
cttaaatttt a                                                           11

<210> SEQ ID NO 28
<211> LENGTH: 18
<212> TYPE: DNA
<213> ORGANISM: Artificial Sequence
```

-continued

```
<220> FEATURE:
<223> OTHER INFORMATION: A synthetic oligonucleotide.
<220> FEATURE:
<221> NAME/KEY: misc_feature
<222> LOCATION: 7
<223> OTHER INFORMATION: N = A, T, G or C

<400> SEQUENCE: 28
cgtctcntat tagtagaa                                                 18

<210> SEQ ID NO 29
<211> LENGTH: 18
<212> TYPE: DNA
<213> ORGANISM: Artificial Sequence
<220> FEATURE:
<223> OTHER INFORMATION: A synthetic oligonucleotide.
<220> FEATURE:
<221> NAME/KEY: misc_feature
<222> LOCATION: 12
<223> OTHER INFORMATION: N = A, T, G or C

<400> SEQUENCE: 29
ttctactaat angagacg                                                 18
```